United States Patent [19]

Aoki et al.

[11] Patent Number: 4,795,484

[45] Date of Patent: * Jan. 3, 1989

[54] HERBICIDAL COMPOSITION CONTAINING A DERIVATIVE OF 1,2,4-TRIAZOLE AS AN ACTIVE INGREDIENT

[75] Inventors: Katsumichi Aoki; Takafumi Shida; Takeo Watanabe; Keigo Satake; Hiroyasu Shinkawa; Shiro Yamazaki, all of Iwaki, Japan

[73] Assignee: Kureha Kagaku Kogyo Kabushiki Kaisha, Tokyo, Japan

[*] Notice: The portion of the term of this patent subsequent to Jan. 8, 2002 has been disclaimed.

[21] Appl. No.: 858,531

[22] Filed: Apr. 24, 1986

Related U.S. Application Data

[63] Continuation of Ser. No. 487,742, Apr. 22, 1983, abandoned.

[30] Foreign Application Priority Data

May 7, 1982 [JP] Japan .................................. 57-77010
Nov. 25, 1982 [JP] Japan ................................ 57-206486

[51] Int. Cl.$^4$ .................. A01D 43/64; C07D 249/10
[52] U.S. Cl. ......................................... 71/92; 548/262
[58] Field of Search ............................. 71/92; 548/262

[56] References Cited

U.S. PATENT DOCUMENTS 3,681,374  8/1972  Yado et al. .......................... 548/262
4,280,831  7/1981  Patel ....................................... 71/92
4,492,597  1/1985  Aoki et al. ............................. 71/92

FOREIGN PATENT DOCUMENTS 0034481  2/1981  European Pat. Off. .
0070089  1/1983  European Pat. Off. .

OTHER PUBLICATIONS

Chemical Abstracts, vol. 86, No. 11, Mar. 14, 1977, p. 619, No. 72658a. (Japanese Patent Laid-Open No. 88968/1976).
Browne, E. J. and Polya, J. B., Triazoles Part VI, 1,5-Diaryl-1,2,4-Triazole-3-Aldehydes, Feb., 1962, pp. 575-583 in Journal of the Chemical Society.
Sawdey, Rearrangement of 4-Arylazo-2-Phenyloxazolin-5-ones: A new Synthesis of 1H-1,2,4-Triazoles, Apr. 20, 1957, pp. 1955-1956 in Journal of the American Chemical Society, vol. 70.
Harhash, A. H., Elnagdi, M. H. Elbanani, A. A. A., Synthesis of Some Triazolyoxazolines and Triazolylenzoxazones, 1975, in Tetrahedron, vol. 31.

Primary Examiner—Catherine L. Mills
Attorney, Agent, or Firm—Nixon & Vanderhye

[57] ABSTRACT

Disclosed herein is herbicidal composition comprising a derivative of 1,2,4-triazole as an active ingredient, represented by the general formula (I):

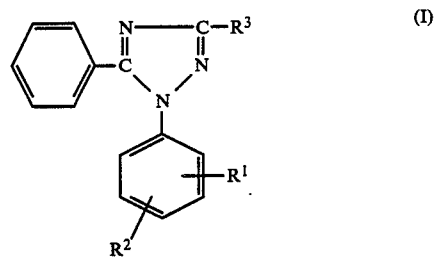

wherein $R^1$ represents a hydrogen atom, a halogen atom or a $C_1$-$C_2$) alkyl group; $R^2$ represents a hydrogen atom, a halogen atom, a ($C_1$-$C_2$) alkyl group fluoromethyl group (—CH$_2$F),3,3,3-trifluoropopyl group, methoxy group, cyano group, methoxymethyl group, methylthio group, methoxycarbonyl group or isopropoxycarbonyl group and $R^3$ represents a thiocarbamoyl group or a group represented by the general formula (II):

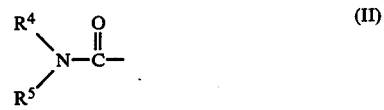

wherein $R^4$ represents a hydrogen atom, a ($C_1$-$C_2$) alkyl
(Abstract continued on next page.)

group or a hydroxy ($C_1$-$C_2$) alkyl group and $R^5$ represents a hydrogen atom, a $C_1$-$C_2$) alkyl group, halogeno ($C_1$-$C_2$) alkyl group, hydroxy ($C_1$-$C_2$) alkyl group, cyanomethyl group, acetyl group, halogenoacetyl group, methoxyacetyl group, amino group, phenyl group, methoxy group, hydroxyl group, ($C_2$-$C_3$) alkenyl group, halogeno ($C_2$-$C_3$) alkenyl group, isopropylcarbonyl group, methylthiocarbamoyl group or 2-methoxyethyl group, the proviso that $R^2$ is not a hydrogen atom, halogen atom or ($C_1$-$C_2$) alkyl group when both of $R^4$ and $R^5$ represent hydrogen atoms, and herbicidally acceptable carrier(s) or diluent(s).

15 Claims, 27 Drawing Sheets

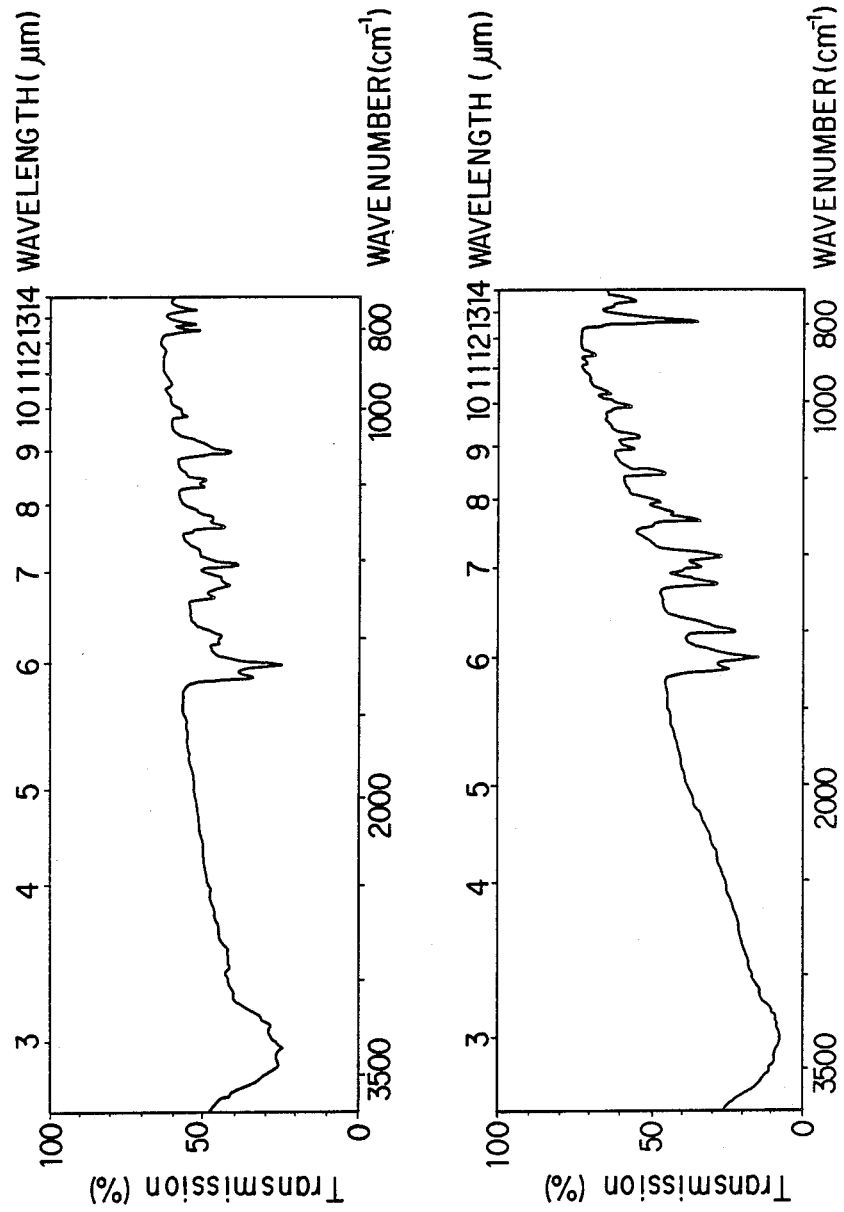

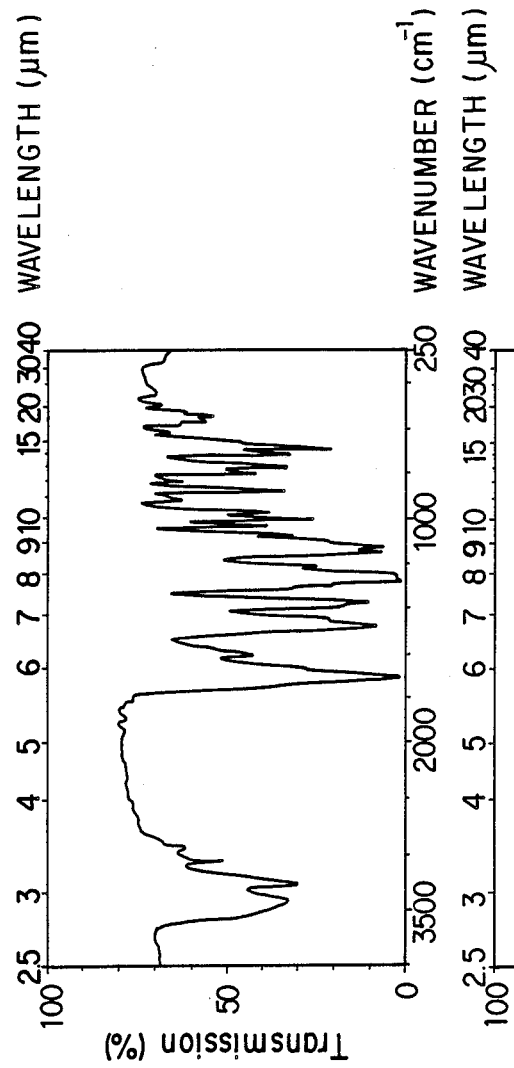
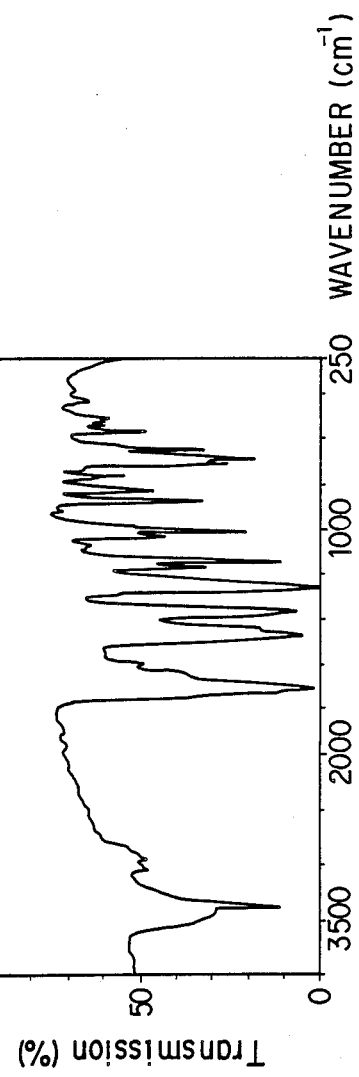
Fig. 43
Fig. 44

HERBICIDAL COMPOSITION CONTAINING A DERIVATIVE OF 1,2,4-TRIAZOLE AS AN ACTIVE INGREDIENT

This application is a continuation of application Ser. No. 487,742 filed Apr. 22, 1983, abandoned.

BACKGROUND OF THE INVENTION

The present invention relates to a herbicidal composition comprising a derivative of 1,2,4-triazole as an active ingredient, represented by the general formula (I):

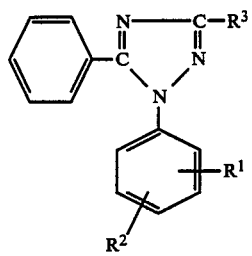

wherein $R^1$ represents a hydrogen atom, a halogen atom or a ($C_1$-$C_2$) alkyl group; $R^2$ represents a hydrogen atom, a halogen atom, a ($C_1$-$C_2$) alkyl group, fluoromethyl group (—$CH_2F$), 3,3,3-trifluoropropyl group, methoxy group, cyano group, methoxymethyl group, methylthio group, methoxycarbonyl group or isopropoxycarbonyl group and $R^3$ represents a thiocarbamoyl group or a group represented by the general formula (II):

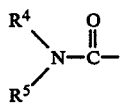

wherein $R^4$ represents a hydrogen atom, a ($C_1$-$C_2$) alkyl group or a hydroxy ($C_1$-$C_2$) alkyl group and $R^5$ represents a hydrogen atom, a ($C_1$-$C_2$) alkyl group, halogeno ($C_1$-$C_2$) alkyl group, hydroxy ($C_1$-$C_2$) alkyl group, cyanomethyl group, acetyl group, halogenoacetyl group, methoxyacetyl group, amino group, phenyl group, methoxy group, hydroxyl group, ($C_2$-$C_3$) alkenyl group, halogeno ($C_2$-$C_3$) alkenyl group, isopropylcarbonyl group, methylthiocarbamoyl group or 2-methoxyethyl group, with the proviso that $R^2$ is not a hydrogen atom, halogen atom or ($C_1$-$C_2$) alkyl group when both of $R^4$ and $R^5$ represent hydrogen atoms, and herbicidally acceptable carrier(s) or diluent(s).

The present inventors have studied for finding a compound showing an excellent activity in selectively controlling weeds such as *Echinochloa crus-galli*, *Poa annua*, *Chenopodium album*, *Cardamine flexuosa*, *Portulaca orelacea*, etc. without any phytotoxicity to crop plants such as rice, wheat and maize, and as a result, they have found that a derivative of 1,2,4-triazole, represented by the general formula(I) shows an excellent herbicidal activity for practically controlling the weeds, and have been attained to the present invention.

DETAILED DESCRIPTION OF THE INVENTION

Figure 1:
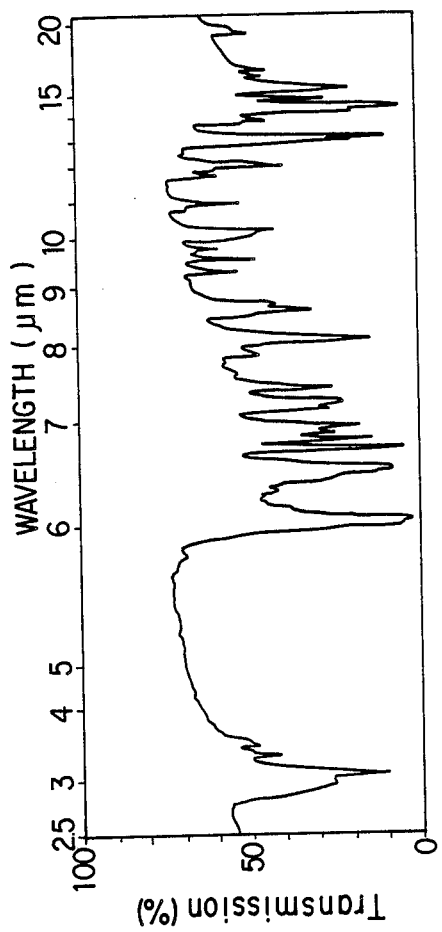

The compounds according to the present invention represented by the general formula(I) show herbicidal activity to broad-leaved plants and graminaceous plants, and exhibit excellent herbicidal activity, particularly to the broad-leaved weeds such as *Portulaca oleracea*, *Chenopodium album*, *Stellaria media*, *Cardamine flexuosa*, etc. in various weed-control tests such as seed germination test, soil-treatment test and foliar application test, etc. without causing any phytotoxicity to useful plants such as *Oryza sativa*, *Triticum aestivum*, *Zea mais*, etc. The field of application of the compounds according to the present invention (hereinafter referred to as the present compound) covers the application on arable lands such as paddy fields, ordinary crop fields, orchards, etc. and on growing the flowering plants.

The present compounds are synthesizable according to some of the reactions shown by the following reaction formulae (a) to (d).

(1) In the case where $R^3$ represents

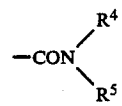

and $R^5$ represents a hydrogen atom, a ($C_1$-$C_2$) alkyl group, halogeno ($C_1$-$C_2$) alkyl group, hydroxy ($C_1$-$C_2$) alkyl group, cyanomethyl group, amino group, phenyl group, methoxy group, hydroxyl group, ($C_2$-$C_3$) alkenyl group, halogeno ($C_2$-$C_3$) alkenyl group, isopropylcarbonyl group or 2-methoxyethyl group, the present compound is conveniently synthesizable by at first reacting a suitable amino derivative (III) to a derivative of 4-phenylhydrazono-2-phenyloxazoline-5-one (IV) in acetone or dioxane and cyclizating the thus obtained compound (V) by the use of hydrochloric acid as are shown in the reaction formula(a).

Reaction formula(a):

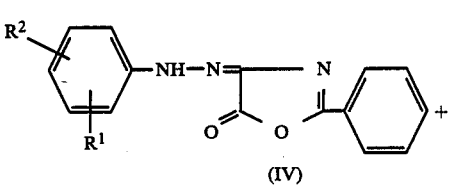

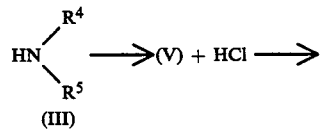

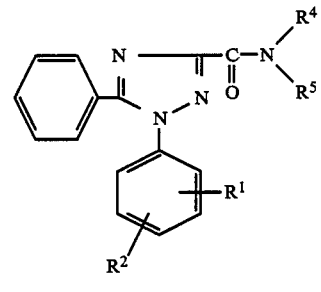

(2) In the case where $R^3$ represents

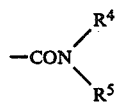

and $R^5$ represents acetyl group, halogenoacetyl group, or methoxyacetyl group, the present compound is easily synthesized by acylating a derivative of 1,2,4-triazole(VI) with an acid chloride or an acid anhydride in an inert solvent such as benzene or toluene as is shown in the following reaction formula(b).

Reaction formula(b):

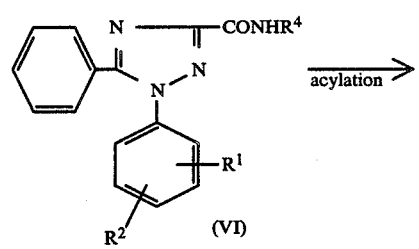

(3) In the case where $R^3$ represents a thiocarbamoyl group, the present compound is synthesized by reacting a cyano derivative of 1,2,4-triazole(VII) with hydrogen sulfide in methanol in which ammonia has been absorbed as shown in the following reaction formula(c).

Reaction formula(c):

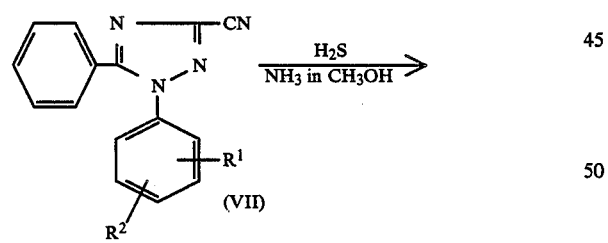

(4) In the case where $R^3$ represents a group

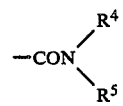

and $R^5$ represents a methythiocarbamoyl group, the present compound is synthesized by reacting a derivative of 1,2,4-triazole(VIII) with N-methylthiourea in a solvent such as benzene and toluene as is shown in the following reaction formula(d).

Reaction formula(d):

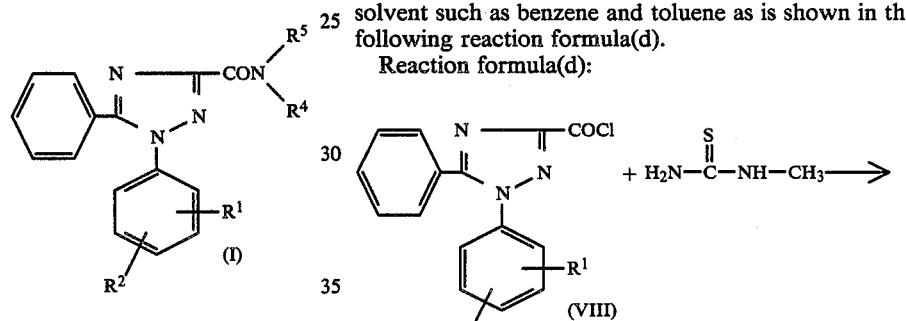

The concrete examples of the present compounds and their physicochemical properties are shown in Table 1.

TABLE 1

| No. of compound | Substituents in General formula (I) | | | Appearance | Melting Point (°C.) | Yield (%) |
| --- | --- | --- | --- | --- | --- | --- |
| | $R^1$ | $R^2$ | $R^3$ | | | |
| 1 | H | H | —CONHCH$_3$ | pale yellow cryst. | 158–159 | 63.5 |
| 2 | H | 3-CH$_3$ | —CONHCH$_3$ | colorless cryst. | 135–136 | 61.7 |
| 3 | H | 3-CH$_3$ | —CONH—C$_6$H$_5$ | pale yellow cryst. | 204–206 | 66.7 |
| 4 | H | 3-CH$_3$ | —CONHCH$_2$CH$_2$Cl | colorless cryst. | 126–128 | 64.6 |
| 5 | H | 3-CH$_3$ | —CONHCH$_2$CH$_2$OH | colorless cryst. | 102–104 | 63.2 |
| 6 | H | 3-CH$_3$ | —CONHCH$_2$CN | pale brown vis.[1] liq.[2] | — | 61.3 |
| 7 | H | 3-CH$_3$ | —CONHOH | pale brown cryst. | 155–158 | 64.6 |
| 8 | H | 3-CH$_3$ | —CONHNH$_2$ | pale yellow cryst. | 52–55 | 62.7 |
| 9 | H | 3-CH$_3$ | —CONHOCH$_3$ | colorless cryst. | 133–135 | 67.2 |
| 10 | H | 3-CH$_3$ | —CON(CH$_3$)$_2$ | colorless cryst. | 130–131 | 63.0 |
| 11 | H | 3-CH$_3$ | —CON(CH$_2$CH$_2$OH)$_2$ | pale brown cryst. | 114–116 | 70.3 |
| 12 | 3-CH$_3$ | 4-CH$_3$ | —CONHCH$_3$ | colorless cryst. | 150–152 | 69.1 |
| 13 | 3-CH$_3$ | 4-CH$_3$ | —CONHCH$_2$CH$_2$OH | pale brown cryst. | 107–109 | 74.0 |

TABLE 1-continued

| No. of compound | \_\_\_Substituents in General formula (I)\_\_\_ | | | Appearance | Melting Point (°C.) | Yield (%) |
|---|---|---|---|---|---|---|
| | R¹ | R² | R³ | | | |
| 14 | 3-CH₃ | 4-CH₃ | —CONHOH | pale brown vis. liq. | — | 73 |
| 15 | 3-CH₃ | 4-CH₃ | —CONHOCH₃ | pale yellow cryst. | 147–149 | 58.7 |
| 16 | 3-CH₃ | 4-CH₃ | —CON(CH₃)₂ | colorless cryst. | 175–176 | 66.0 |
| 17 | 2-CH₃ | 3-Cl | —CONHCH₃ | colorless cryst. | 195–196 | 72.0 |
| 18 | 2-CH₃ | 3-Cl | —CONHCH₂CH₂Cl | colorless cryst. | 140–141 | 61.3 |
| 19 | 2-CH₃ | 3-Cl | —CONHCH₂CH₂OH | pale yellow cryst. | 98–101 | 63.7 |
| 20 | H | H | —CONHCOCCl₃ | colorless cryst. | 162–163 | 63.6 |
| 21 | H | H | —CONHCOCF₃ | colorless cryst. | 125–127 | 42.0 |
| 22 | H | 3-CH₃ | —CONHCOCH₃ | colorless crtst. | 142–144 | 59.7 |
| 23 | H | 3-CH₃ | —CONHCOCH₂OCH₃ | colorless cryst. | 128–130 | 60.0 |
| 24 | H | 3-CH₃ | —CONHCOCH₂Cl | colorless cryst. | 126–128 | 61.3 |
| 25 | H | 3-CH₃ | —CONHCOCHCl₂ | colorless cryst. | 168–170 | 73.0 |
| 26 | H | 3-CH₃ | —CONHCOCCl₃ | colorless cryst. | 161–162 | 75.0 |
| 27 | 2-CH₃ | 3-Cl | —CONHCOCCl₃ | colorless cryst. | 186–188 | 55.0 |
| 28 | H | 3-CH₃ | —CON(CH₃)(COCH₃) | colorless cryst. | 127–128 | 65.0 |
| 29 | H | 3-CH₃ | —CON(CH₃)(C(=O)—CH₂Cl) | colorless cryst. | 149–150 | 67.2 |
| 30 | H | 3-CH₂F | —CONH₂ | colorless cryst. | 137–138 | 55 |
| 31 | H | 3-OCH₃ | —CONH₂ | pale orange cryst. | 132–134 | 47 |
| 32 | H | 3-CH₂OCH₃ | —CONH₂ | colorless cryst. | 124–126 | 63 |
| 33 | H | 3-SCH₃ | —CONH₂ | pale brown cryst. | 167–168 | 64 |
| 34 | H | 3-CN | —CONH₂ | pale orange cryst. | 195–196 | 56 |
| 35 | H | 3-COOCH₃ | —CONH₂ | pale brown cryst. | 169–170 | 70 |
| 36 | H | 3-COOCH(CH₃)₂ | —CONH₂ | colorless cryst. | 170–172 | 59 |
| 37 | H | 3-CH₂CH₂CF₃ | —CONH₂ | pale yellow cryst. | 176–177 | 63 |
| 38 | 5-CH₃ | 2-OCH₃ | —CONH₂ | colorless cryst. | 212–213 | 67 |
| 39 | H | 3-CH₃ | —CSNH₂ | pale yellow cryst. | 154–156 | 22 |
| 40 | H | 3-CH₂CH₂CF₃ | —C(=O)—NH—C(=O)—CH₃ | colorless cryst. | 148–150 | 75 |
| 41 | 4-CH₃ | 3-CH₃ | —C(=O)—NH—C(=O)—CH₃ | colorless cryst. | 154–156 | 54 |
| 42 | 3-Cl | 2-CH₃ | —C(=O)—NH—C(=O)—CH₃ | colorless cryst. | 160–162 | 65 |
| 43 | H | 3-CH₃ | —C(=O)—NH—C(=O)—CH(CH₃)₂ | colorless cryst. | 170–171 | 66 |
| 44 | 4-CH₃ | 3-CH₃ | —C(=O)—NH—C(=O)—CCl₃ | colorless cryst. | 129–131 | 41 |
| 45 | H | 3-CH₃ | —C(=O)—NH—C(=O)—CF₃ | colorless cryst. | 126–128 | 90 |
| 46 | H | 3-CH₃ | —C(=O)—NH—C(=S)—NHCH₃ | colorless cryst. | 185–187 | 52 |
| 47 | H | 3-CH₃ | —C(=O)—NH—C₂H₅ | pale orange cryst. | 102–104 | 40 |
| 48 | H | 3-CH₃ | —C(=O)—NHCH₂CF₃ | colorless cryst. | 139–140 | 56 |
| 49 | H | 3-CH₃ | —C(=O)—NHCH₂CH=CH₂ | colorless cryst. | 118–119 | 32 |
| 50 | H | 3-CH₃ | —C(=O)—NHCH₂CH₂OCH₃ | colorless cryst. | 63–65 | 23 |

TABLE 1-continued

| No. of compound | \multicolumn{3}{c}{Substituents in General formula (I)} | Appearance | Melting Point (°C.) | Yield (%) |
| --- | --- | --- | --- | --- | --- | --- |
|  | R¹ | R² | R³ |  |  |  |
| 51 | H | 3-CH₃ | 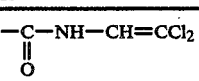 | colorless oil | — | 46 |

Figure 2:
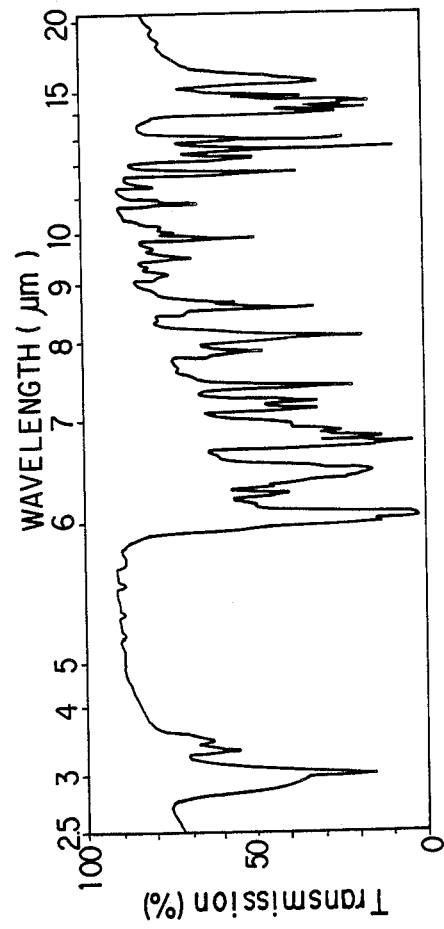
Figure 3:
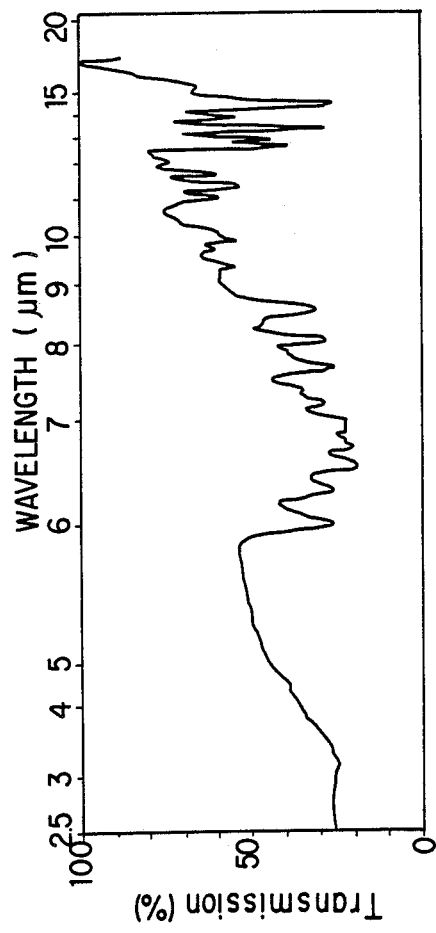
Figure 4:
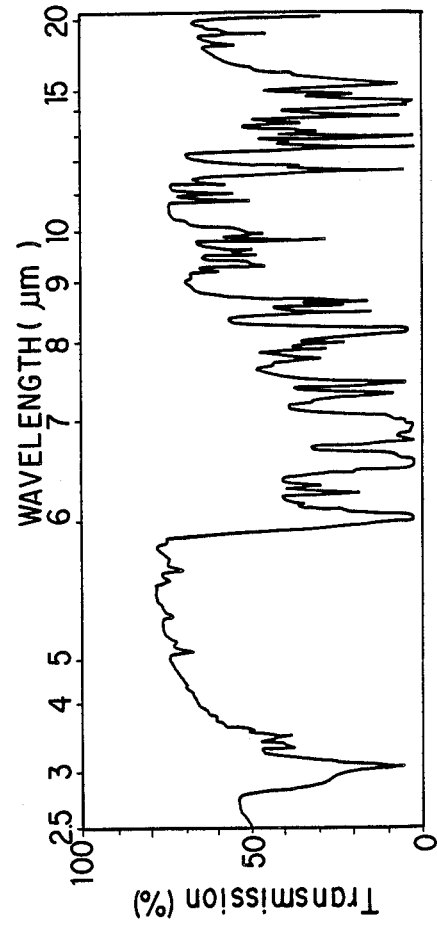
Figure 5:
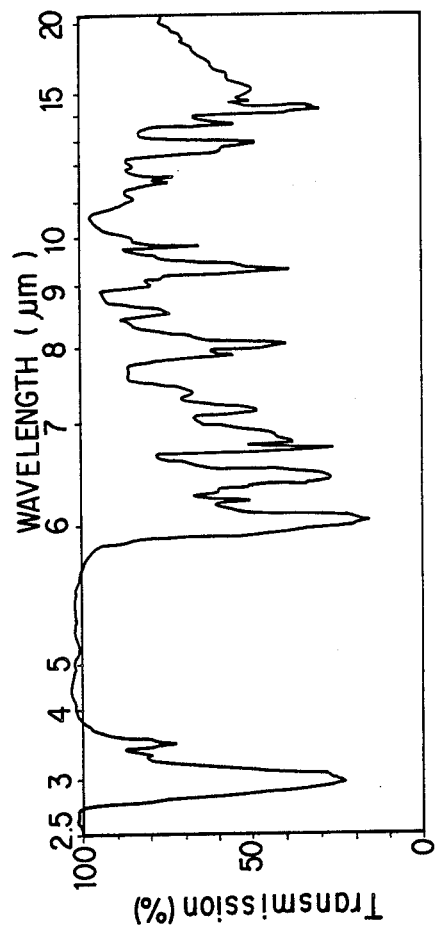
Figure 6:
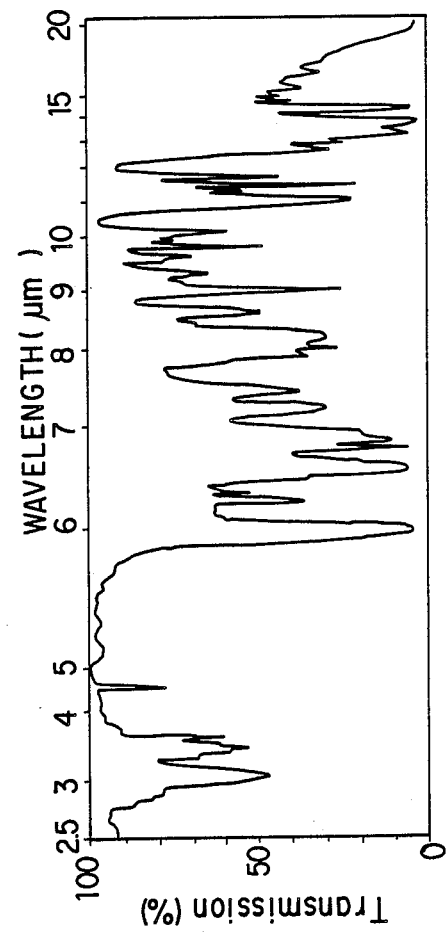
Figure 7:
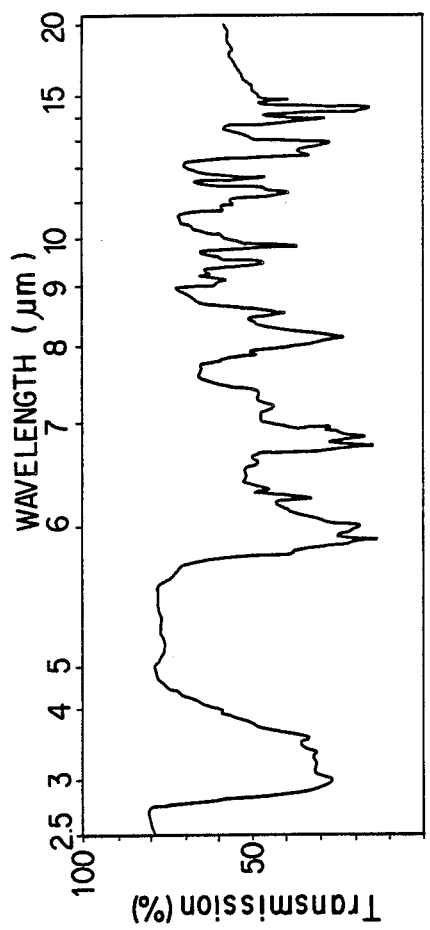
Figure 8:
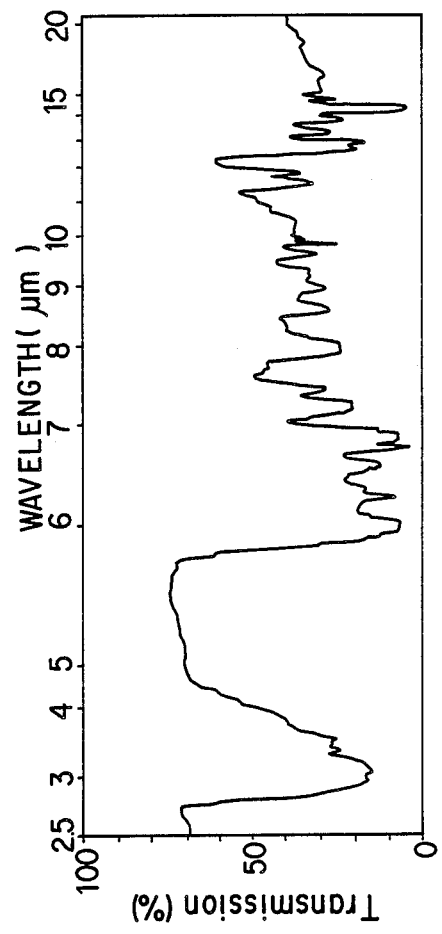
Figure 9:
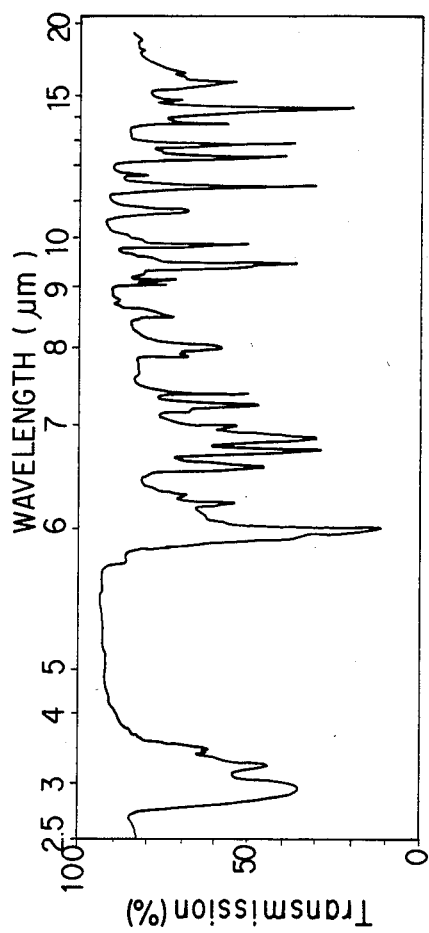
Figure 10:
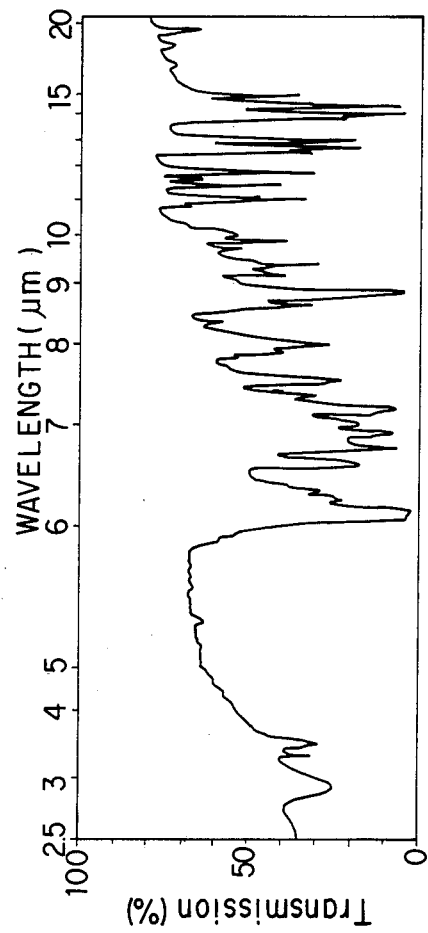
Figure 11:
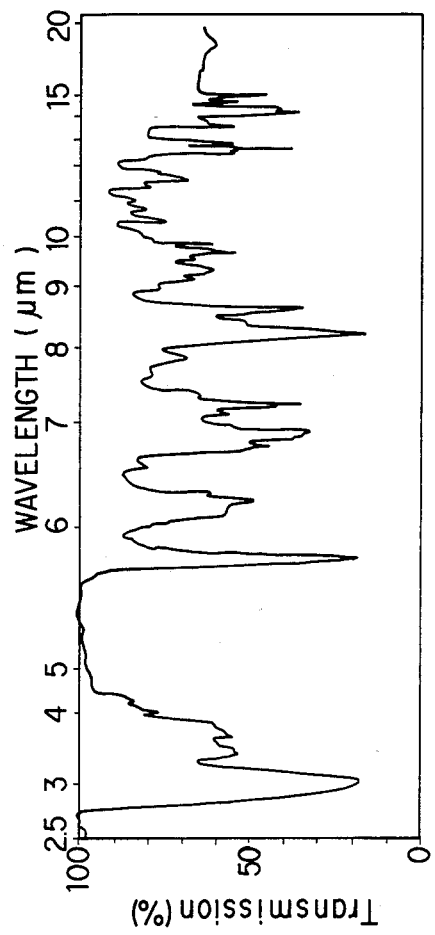
Figure 12:
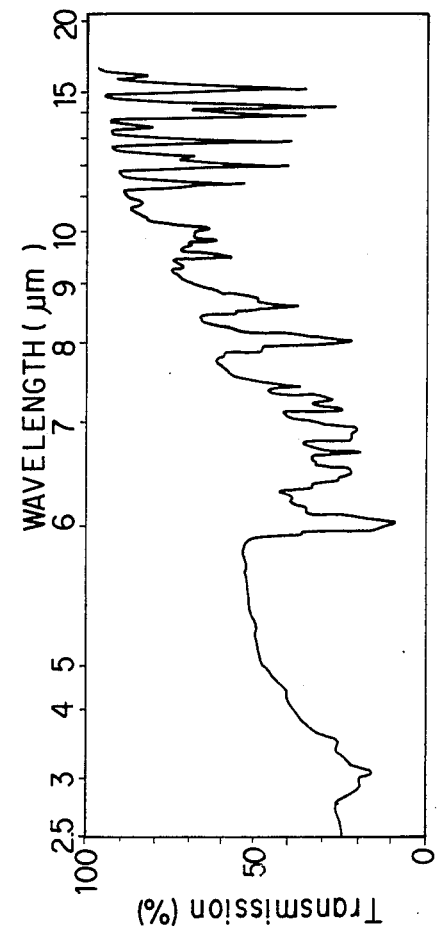
Figure 13:
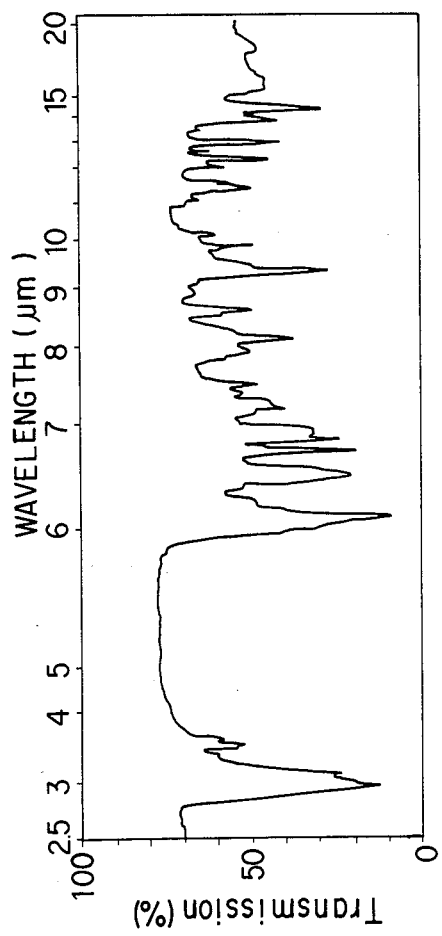
Figure 14:
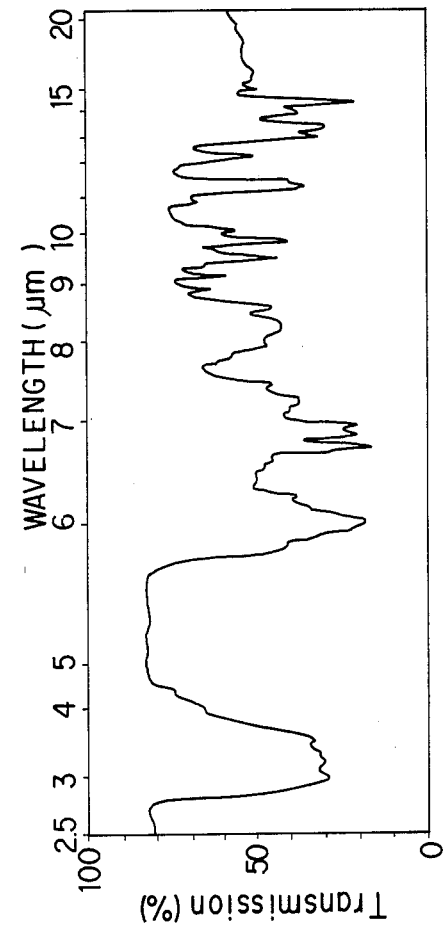
Figure 15:
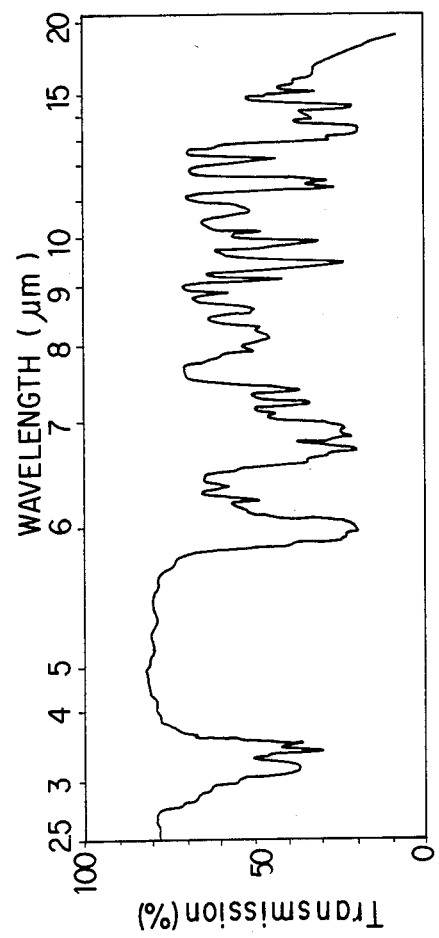
Figure 16:
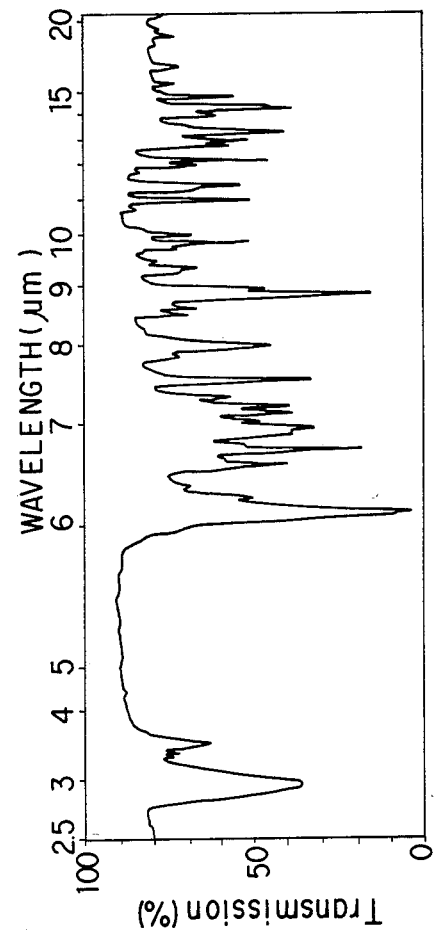
Figure 17:
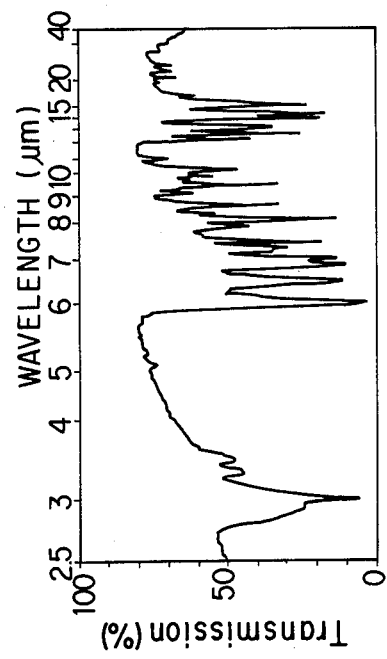
Figure 18:
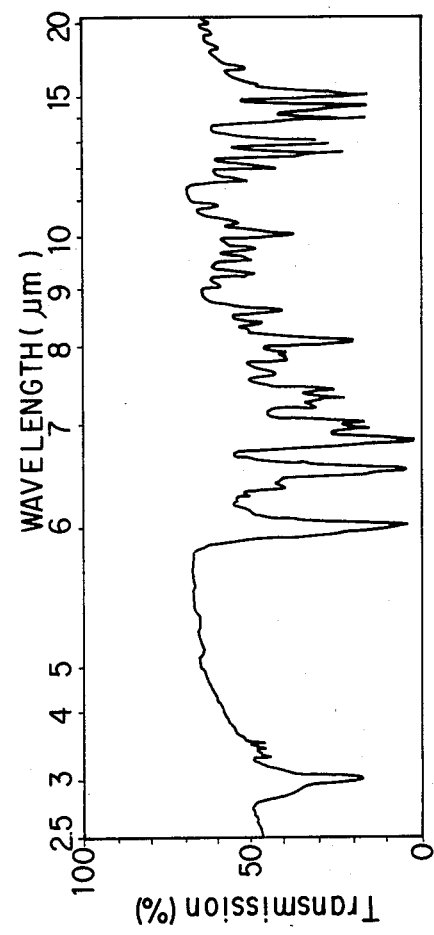
Figure 19:
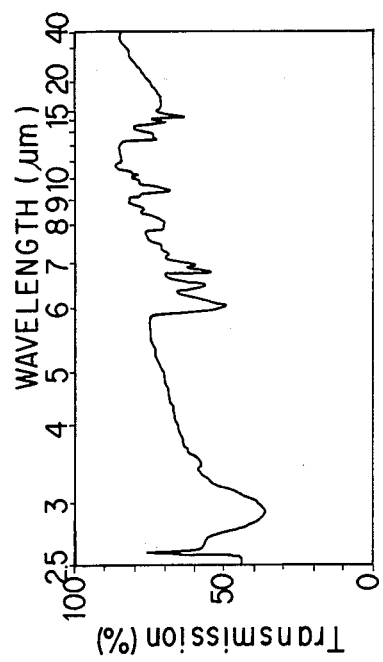
Figure 20:
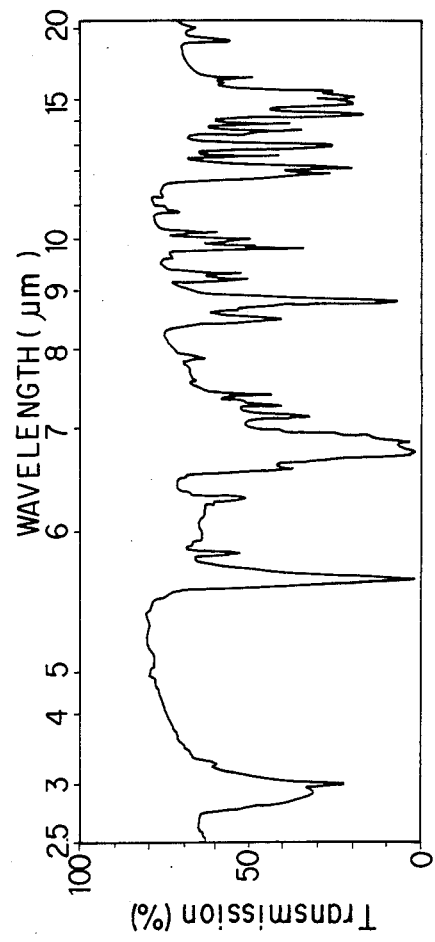
Figure 21:
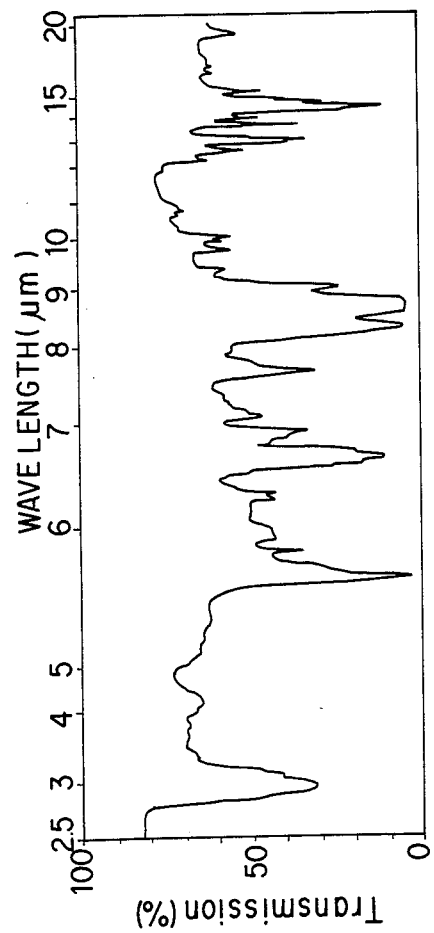
Figure 22:
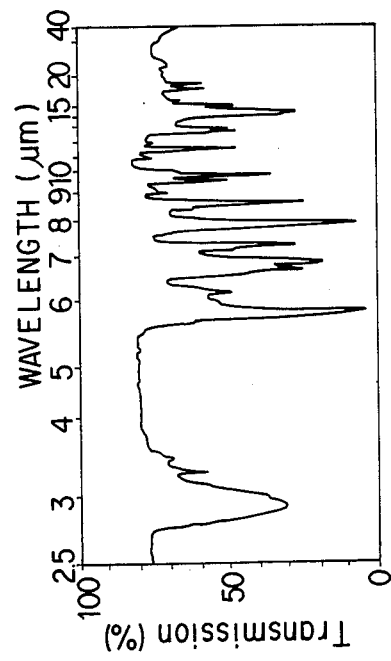
Figure 23:
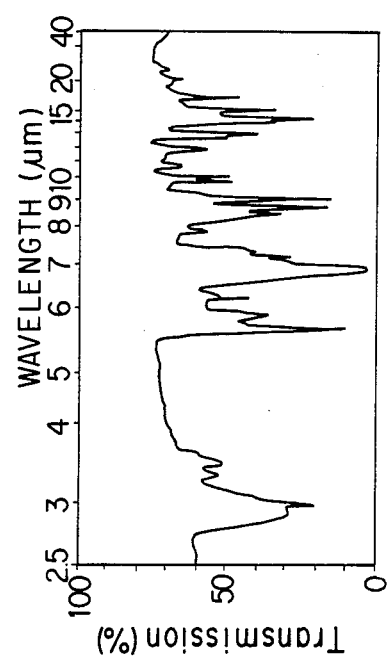
Figure 24:
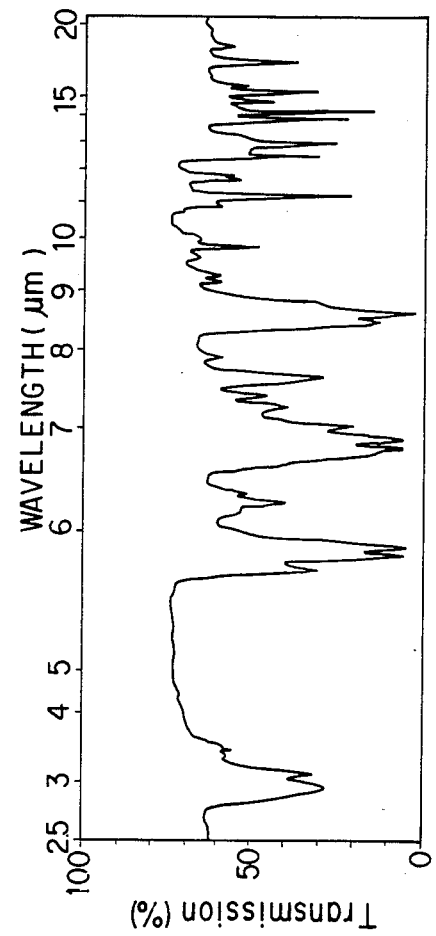
Figures 25, 26:
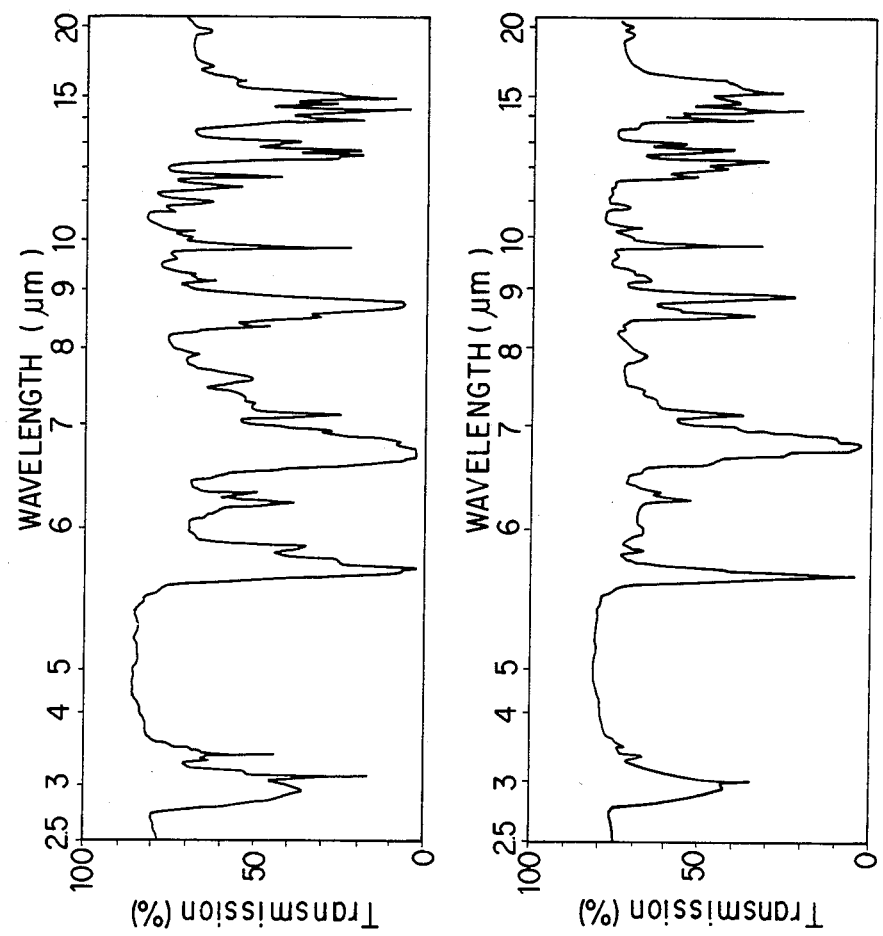
Figure 27:
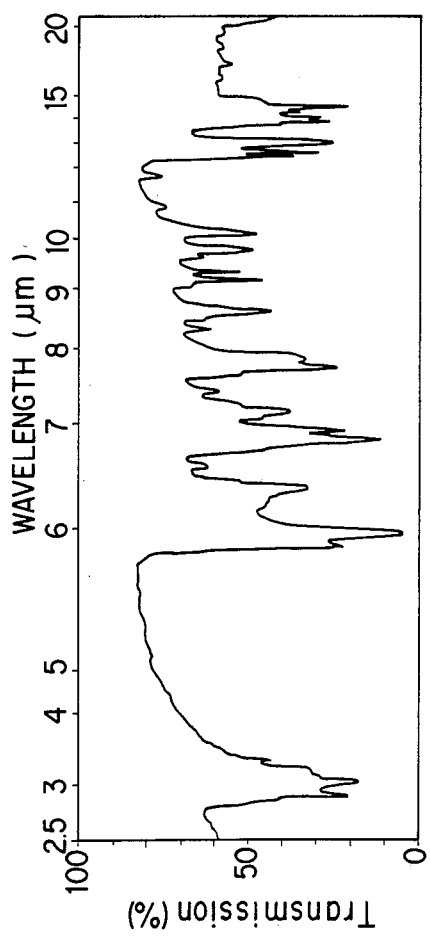
Figure 28:
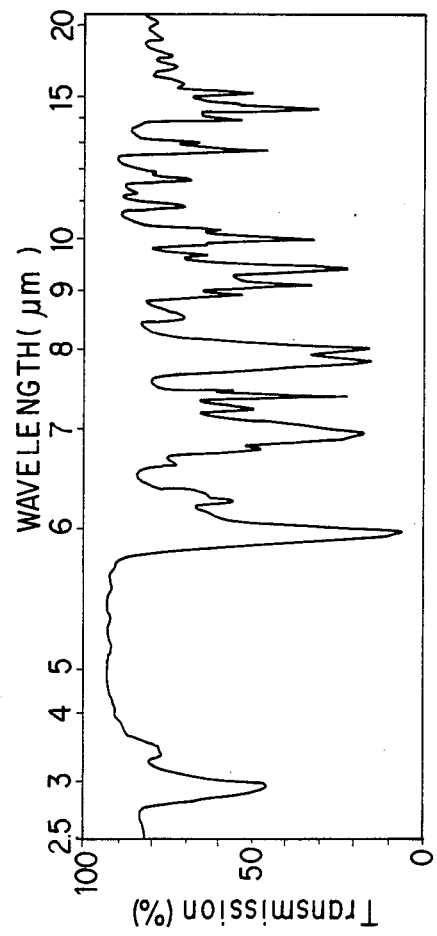
Figure 29:
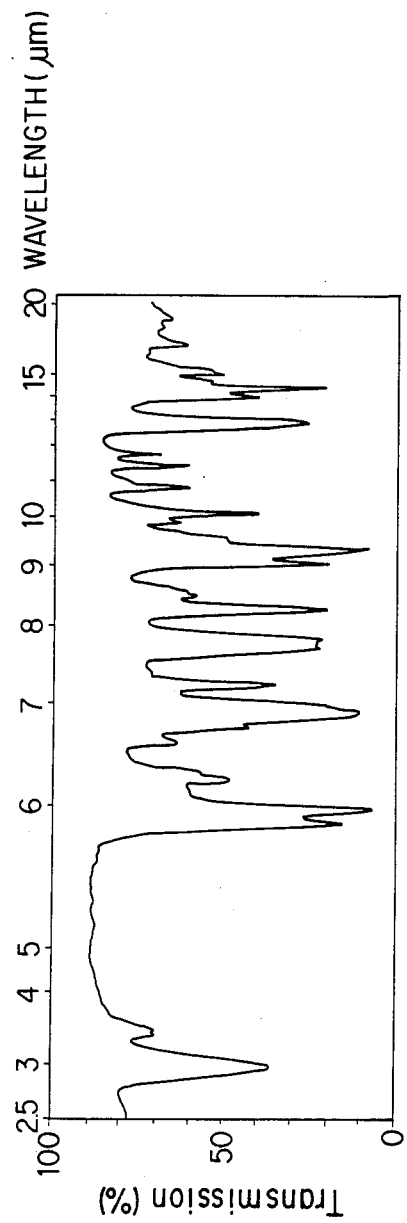
Figure 30:
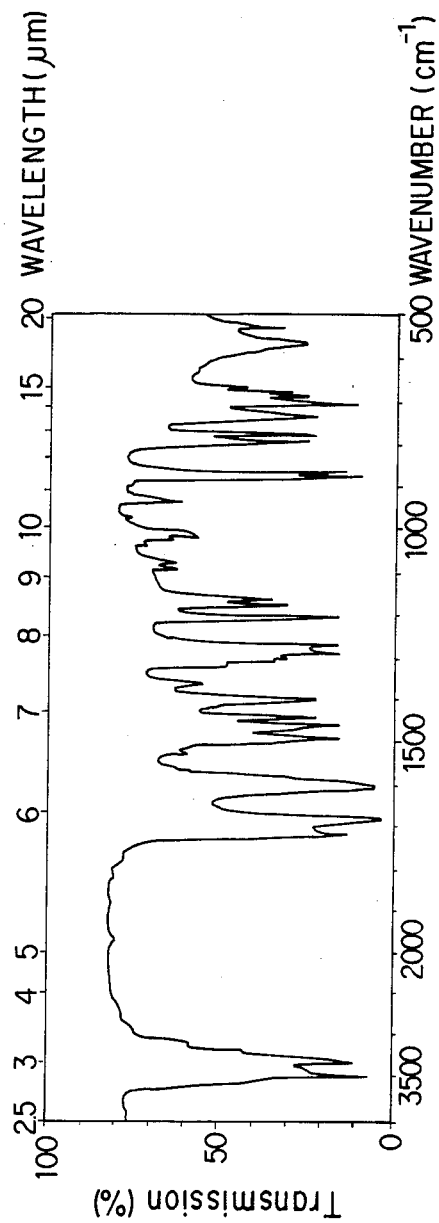
Figures 31, 32:
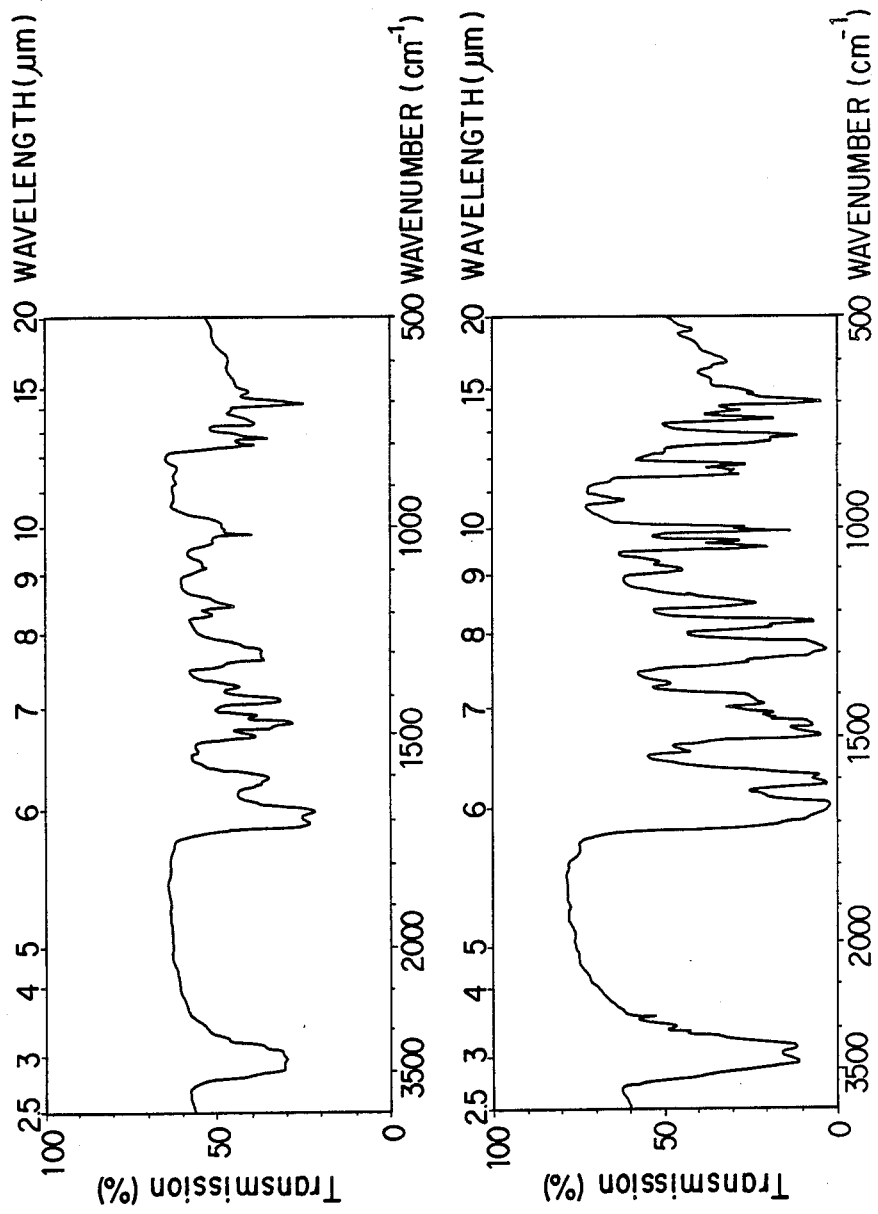
Figures 35, 36:
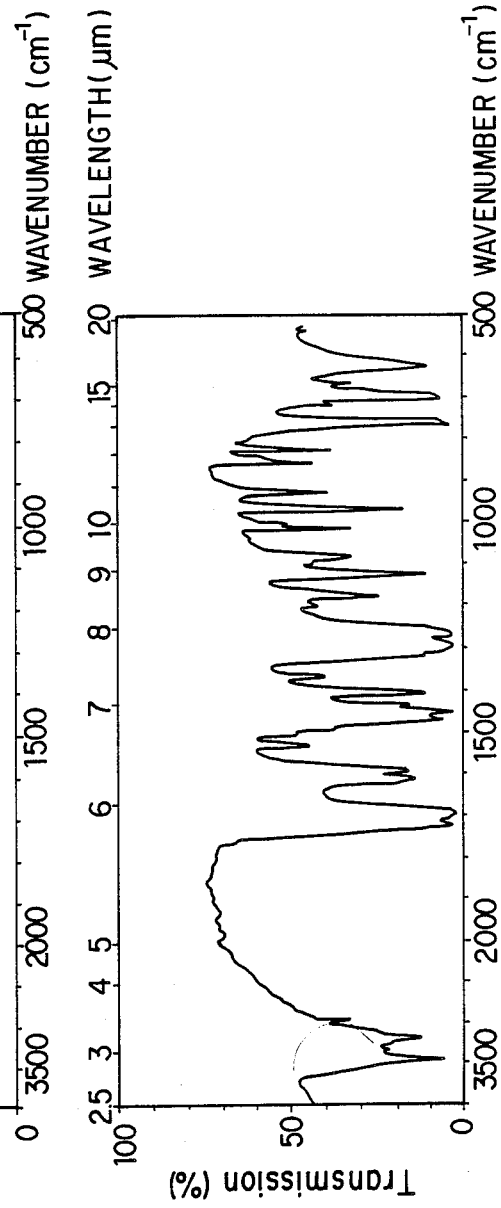
Figure 37:
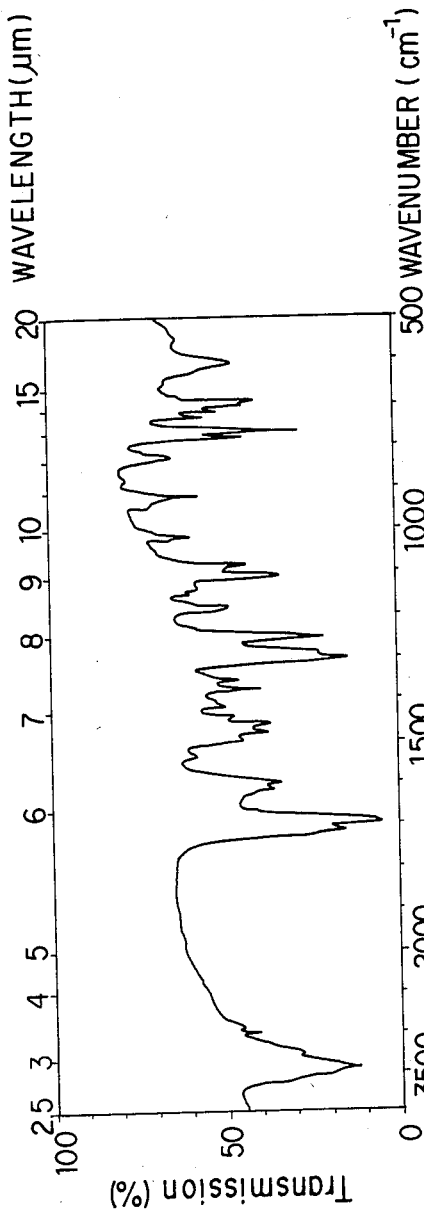
Figure 38:
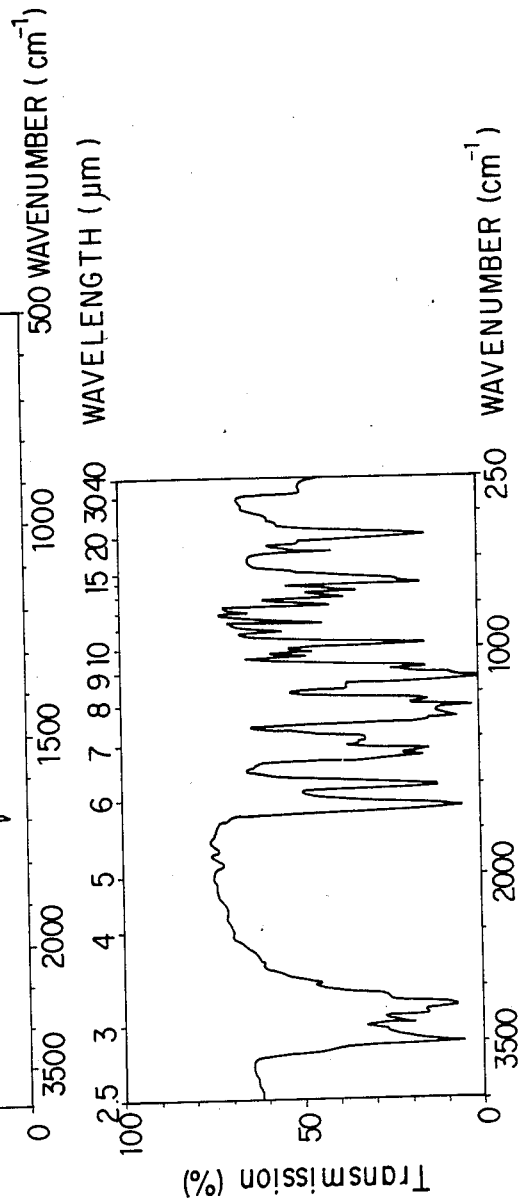
Figures 39, 40:
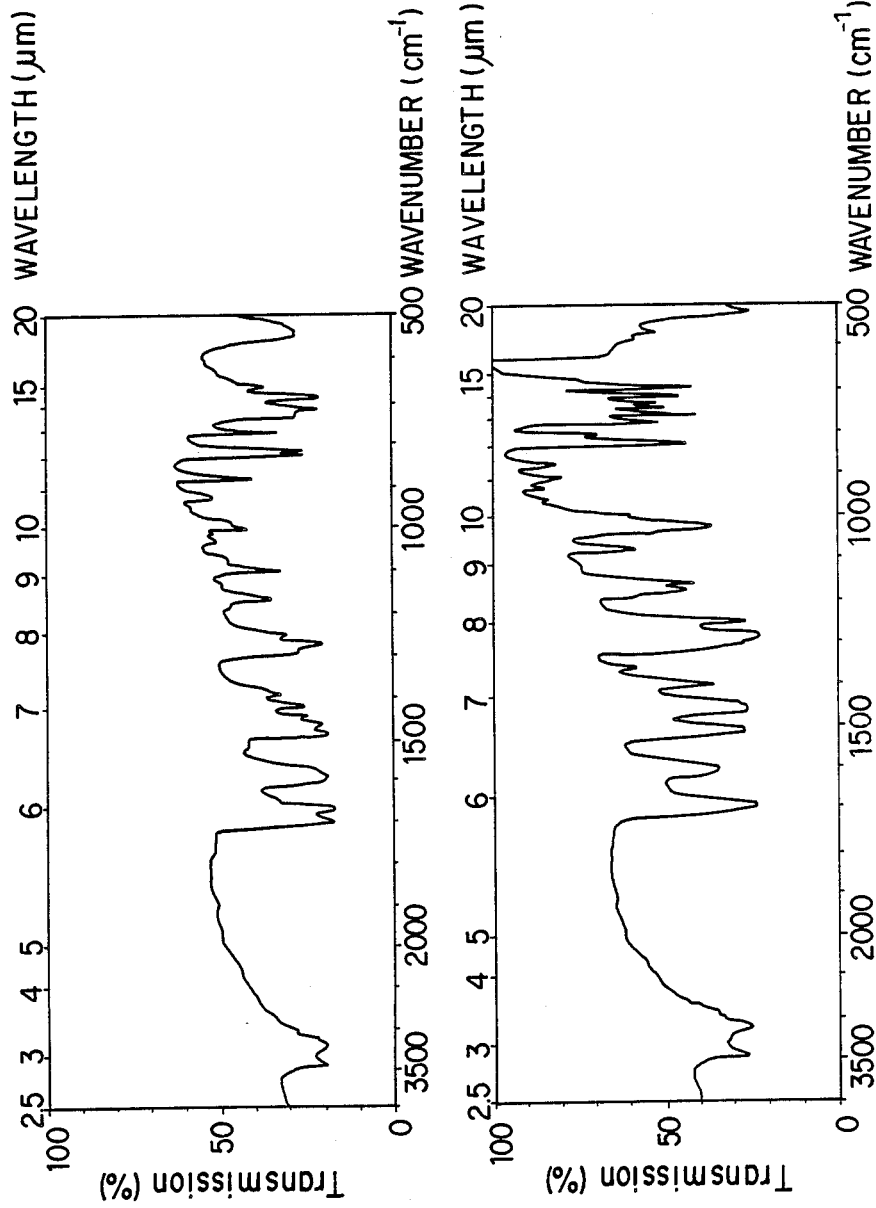
Figures 41, 42:
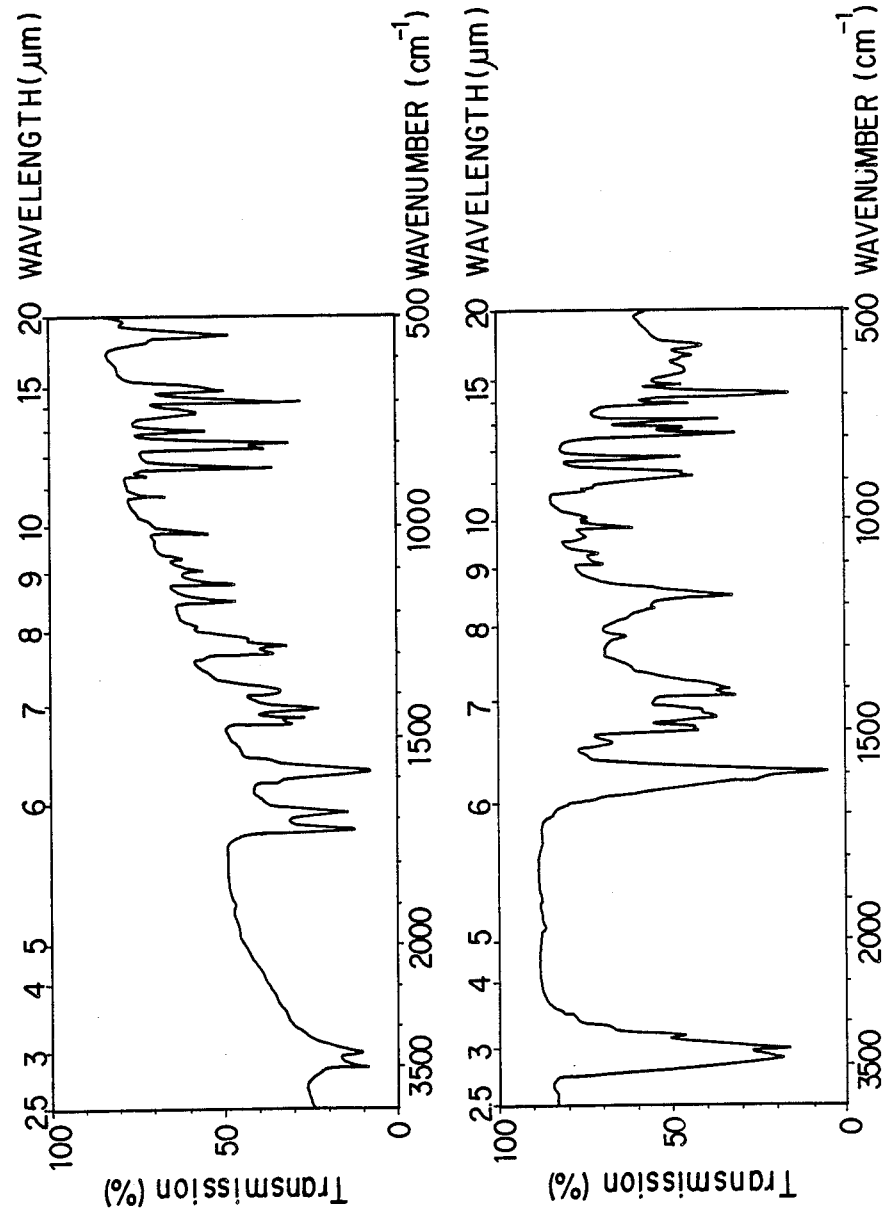
Figure 45:
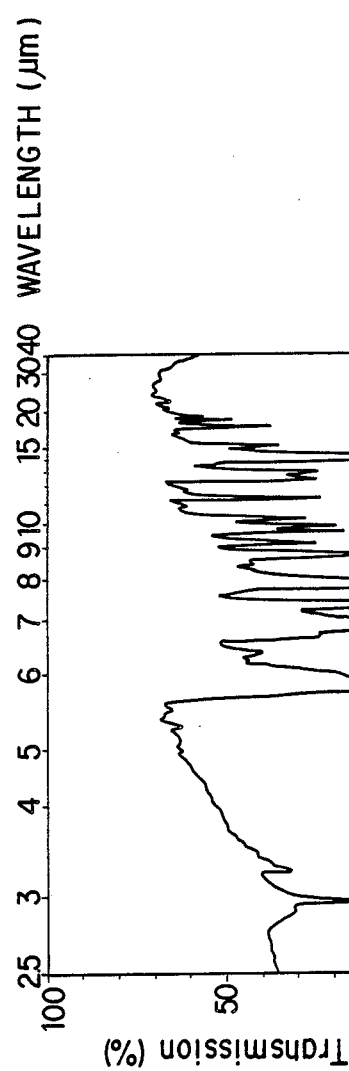
Figure 46:
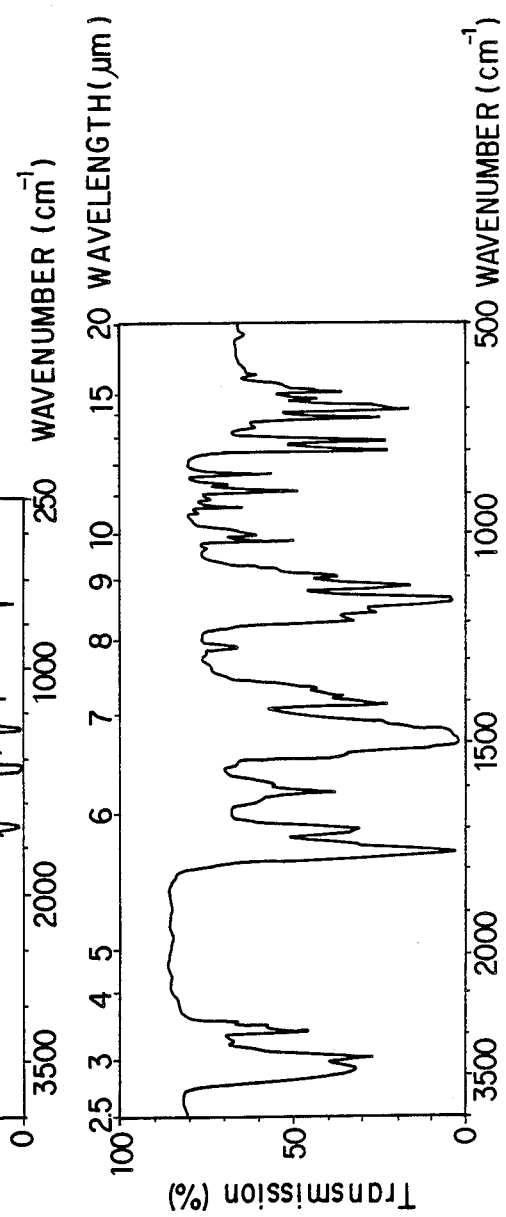
Figure 47:
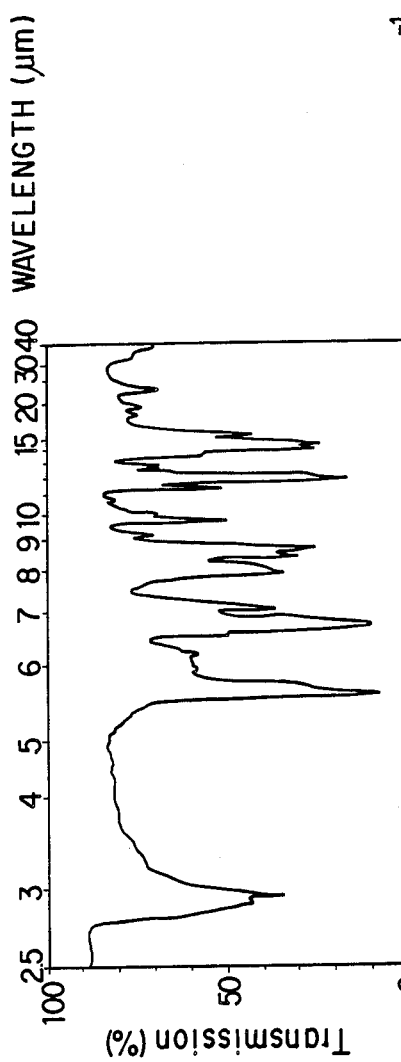
Figure 48:
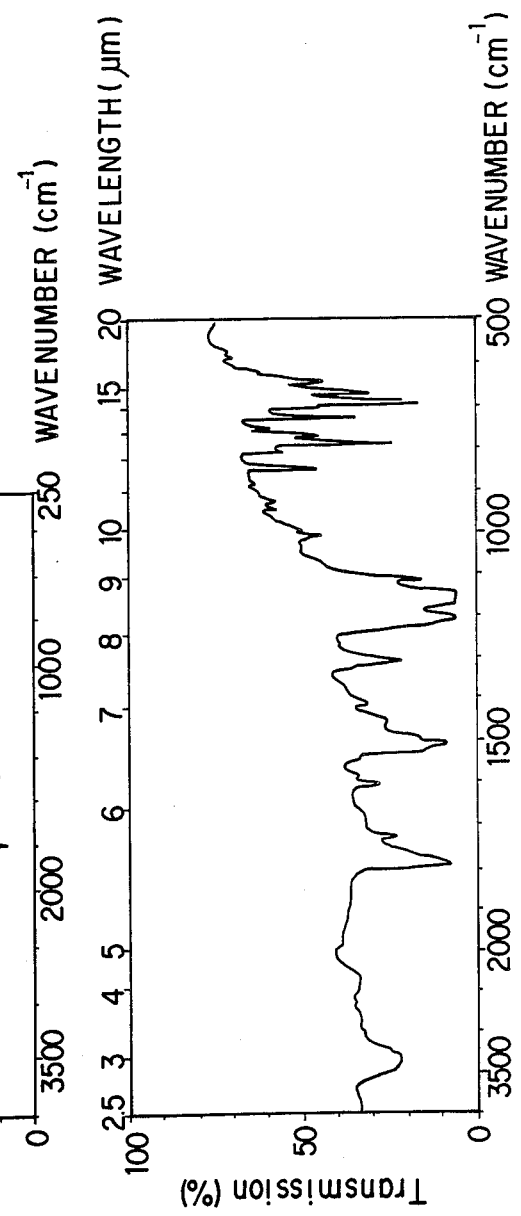
Figures 49, 50:
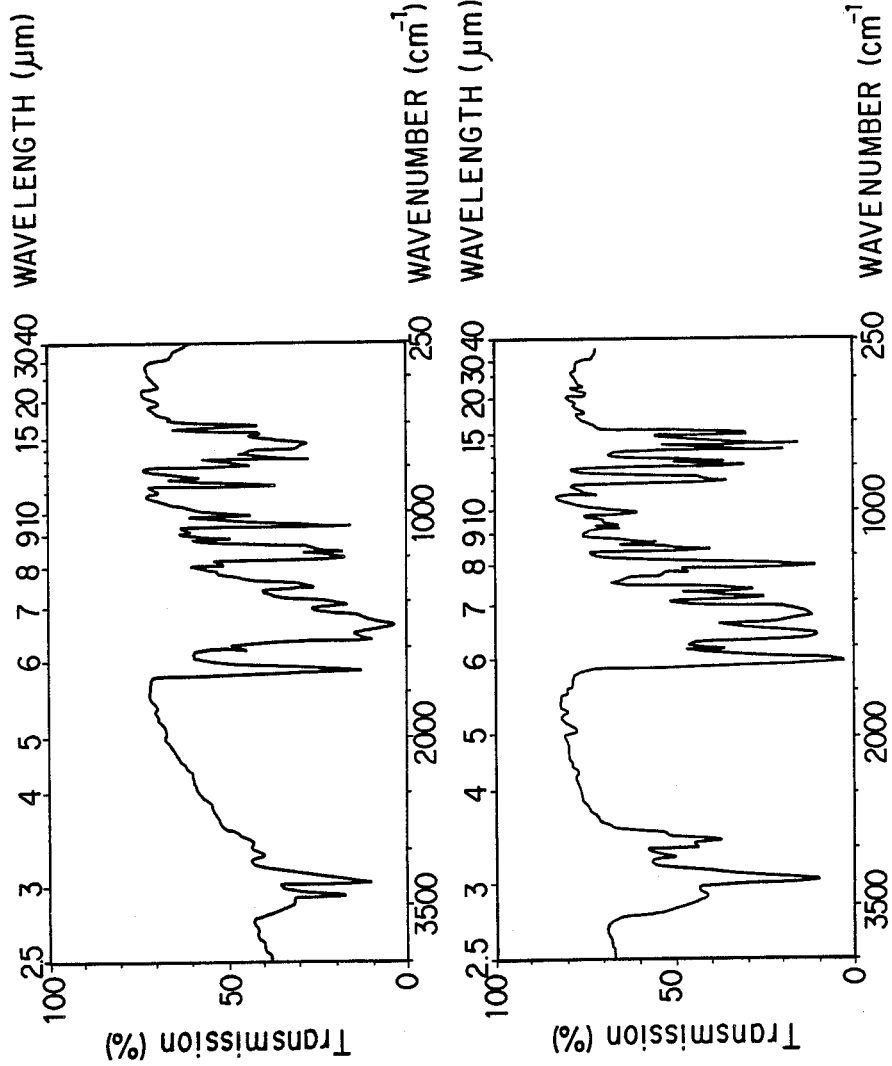
Figures 51, 52:
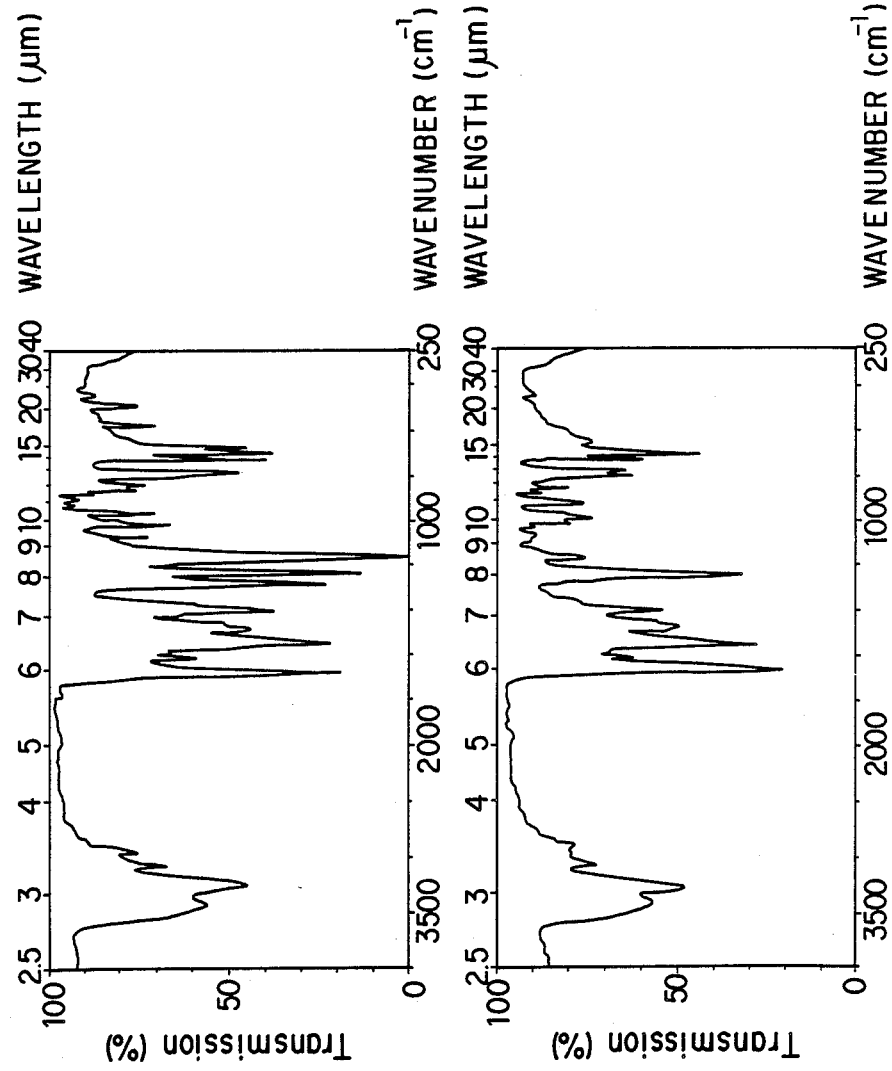
Figure 53:
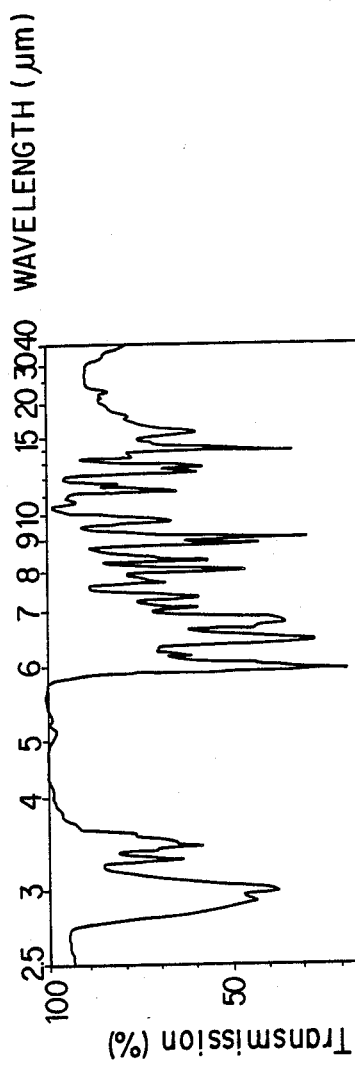
Figure 54:
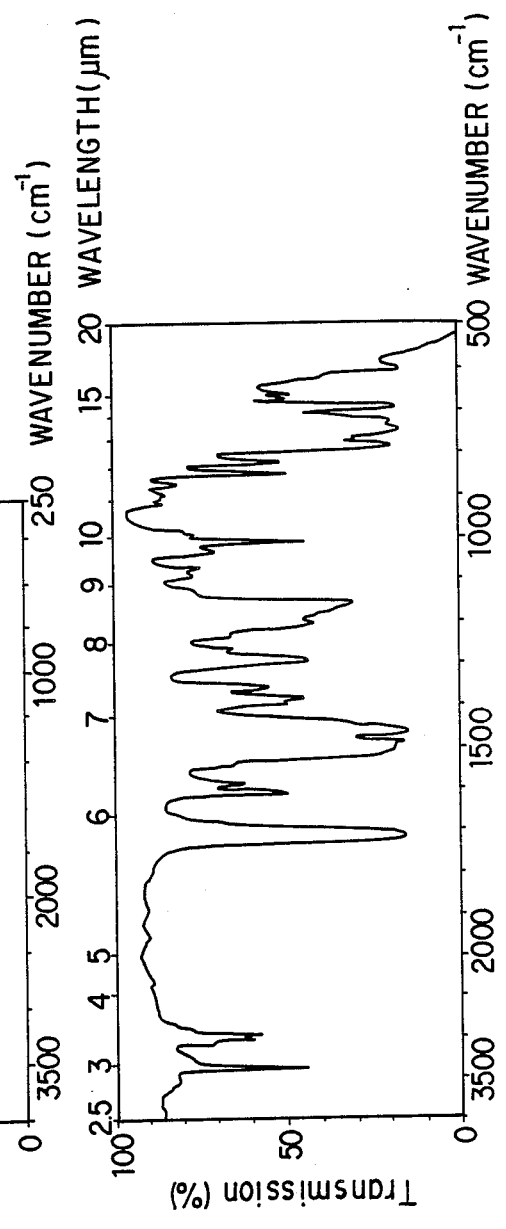

Of the attached drawings, FIGS. 1 to 51 show the infrared absorption spectrum of Compounds Nos. 1 to 51 according to the present invention, respectively.

The following are the synthetic examples of some of the present compounds, the number of each compound corresponding to that shown in Table 1.

SYNTHETIC EXAMPLE 1

Synthesis of Compound No. 2

In 30 ml of acetone, 2.8 g (0.01 mol) of 4-(3-methylphenylhydrazono)-2-phenyloxazoline-5-one (represented by Formula(IV), wherein $R^1$ represents a hydrogen atom and $R^2$ represents a methyl group at 3-position) was suspended, and after adding 1.0 g (0.013 mol) of aqueous 40% solution of methylamine to the suspension, the mixture was heated under a reflux condenser for 30 min. After cooling the reaction mixture, 1.5 ml of conc. hydrochloric acid was added to the reaction mixture drop by drop, and then the mixture was again heated under a reflux condenser for 5 min. After cooling the mixture, the mixture was added into 300 ml of water. The thus separated solid substance was collected by filtration and recrystallized from aqueous ethanolic solution (ethanol:water=10:2 by volume) to obtain 1.8 g of colorless crystals melting at 135° to 136° C. in a yield of 61.7%.

SYNTHETIC EXAMPLE 2

Synthesis of Compound No. 3

In 30 ml of dioxan, 2.8 g (0.01 mol) of 4-(3-methylphenylhydrazono)-2-phenyloxazoline-5-one (represented by Formula (IV), wherein $R^1$ represents a hydrogen atom and $R^2$ represents a methyl group at 3-position) was added, and after further adding 1.3 g (0.013 mol) of aniline to the mixture, the whole system was heated under a reflux condenser for 4 hours. After cooling the reaction mixture, 1.5 ml of conc. hydrochloric acid was added drop by drop to the mixture, and after further heating the mixture for 5 min. at 40° C. and cooling the mixture, the mixture was added into 50 ml of water. The thus separated solid substance was collected by filtration and recrystallized from a mixture of 40 ml of ethanol and 20 ml of dioxan to obtain 2.4 g of pale yellow crystals melting at 204° to 206° C. in a yield of 66.7%.

SYNTHETIC EXAMPLE 3

Synthesis of Compound No. 7

In 20 ml of dioxan, 2.8 g (0.01 mol) of 4-(3-methylphenylhydrazono)-2-phenyloxazoline-5-one (represented by formula (IV), wherein $R^1$ represents a hydrogen atom and $R^2$ represents a methyl group at 3-position) was added, and after adding 0.9 g (0.013 mol) of hydroxylamine hydrochloride to the mixture at a room temperature, 3 ml of aqueous solution containing 0.5 g (0.013 mol) of sodium hydroxide was added to the mixture drop by drop. Then, the mixture was heated for 30 min. under a reflux condenser. After an additional heating for 5 min. at 40° C., the reaction mixture was cooled and then was added into 200 ml of water. The thus separated solid substance was collected by filtration and washed with a mixture of acetone and water to obtain 1.9 g of pale brown crystals melting at 155° to 158° C. in a yield of 64.6%.

SYNTHETIC EXAMPLE 4

Synthesis of Compound No. 26

In 50 ml of toluene, 2.8 g (0.01 mol) of 1-(3-methylphenyl)-5-phenyl-1,2,4-triazole-3-carboxamide (represented by Formula(VI), wherein $R^5$ and $R^2$ represent a hydrogen atom, respectively and $R^1$ represents a methyl group at 3-position) was suspended, and after adding 2.2 g (0.012 mol) of trichloroacetyl chloride to the suspension, the mixture was heated for 2 hours under a reflux condenser. After condensing the reaction mixture, the residue was washed with a small amount of ethanol to obtain 2.5 g of colorless crystals melting at 161° to 162° C. in a yield of 75.0%.

SYNTHETIC EXAMPLE 5

Synthesis of Compound No. 23

In the same manner as in Synthetic Example 4 except for adding 1.3 g (0.012 mol) of methoxyacetyl chloride instead of 2.2 g (0.012 mol) of trichloroacetyl chloride, 2.1 g of colorless crystals melting at 128° to 130° C. was obtained in a yield of 60%.

SYNTHETIC EXAMPLE 6

Synthesis of Compound No. 42

In 100 ml of methanol to which gaseous ammonia had been absorbed, 5.2 g (0.02 mol) of 1-(3-methylphenyl)-3-cyano-5-phenyl-1,2,4-triazole (represented by Formula(VII) wherein $R^1$ is a hydrogen atom and $R^2$ is a methyl group at 3-position) was dissolved, and a reaction was carried out while blowing gaseous $H_2S$ into the solution at 40° to 50° C. for 20 min. After condensing the reaction mixture under a reduced pressure, the condensate was washed with a mixture of hexane and acetone and the residue was recrystallized from a mixture of 30 ml of toluene and 10 ml of hexane to obtain 1.3 g of pale yellow crystals melting at 154° to 156° C. in a yield of 22%.

SYNTHETIC EXAMPLE 7

Synthesis of Compound No. 43

In 30 ml of acetic anhydride, 3.6 g (0.01 mol) of 1-3-(3,3,3-trifluoropropyl)phenyl-5-phenyl-1,2,4-triazole-3-carboxamide was heated under a reflux condenser to react for 2 hours. After condensing the reaction mixture under a reduced pressure, the residue was recrystallized from a mixture of 30 ml of toluene and 10 ml of hexane to obtain 3.0 g of colorless crystals melting at 148° to 150° C. in a yield of 75%.

SYNTHETIC EXAMPLE 8

Synthesis of Compound No. 49

In 50 ml of toluene, 3.0 g (0.01 mol) of 1-(3-methylphenyl)-5-phenyl-1,2,4-triazole-3-carboxylic amide chloride was added, and after adding 0.9 g (0.01 mol) of N-methylthiourea to the mixture, the whole system was heated under a reflux condenser to react for 1 hour. After condensing the reaction mixture under a reduced pressure, the condensate was washed with acetone and recrystallized from toluene to obtain 1.8 g of colorless crystals melting at 185° to 187° C. in a yield of 52%.

FORMULATION EXAMPLE 1

Preparation of a Wettable Powder

The following components were mixed and pulverized to be a wettable powder, and it was applied after diluting with water:
- 50 parts by weight of Compound No. 3,
- 5 parts by weight of a ligninsulfonate,
- 3 parts by weight of an alkylsulfonate and
- 42 parts by weight of diatomaceous earth.

FORMULATION EXAMPLE 2

Preparation of a Wettable Powder

The following components were mixed and pulverized to be a wettable powder, and it was applied after diluting with water:
- 50 parts by weight of Compound No. 32,
- 5 parts by weight of a ligninsulfonate,
- 3 parts by weight of an alkylsulfonate and
- 42 parts by weight of diatomaceous earth.

FORMULATION EXAMPLE 3

Preparation of an Emulsifiable Concentrate

The following components were uniformly mixed together to be an emulsifiable concentrate, and it was applied after diluting with water to be an emulsion:
- 25 parts by weight of Compound No. 10,
- 65 parts by weight of xylene and
- 10 parts by weight of polyoxyethylene alkyl aryl ether.

FORMULATION EXAMPLE 4

Preparation of a Granular Composition

The following components were uniformly mixed, and after adding water to the mixture and kneading the whole system, it was processed into granular form by an extruding granulator and dried to be a granular composition:
- 8 parts by weight of Compound No. 12,
- 40 parts by weight of bentonite,
- 45 parts by weight of clay and
- 7 parts by weight of a ligninsulfonate.

EXAMPLE 1

Herbicidal Test by Application of Candidate Herbicides onto Soil before Germination of Seeds sown therein After packing a planter of the dimensions of 650×210×200 mm with garden soil in a crop field condition, sowing a predetermined amount of the seeds of plants to be tested thereon and covering the seeds with soil, each of the aqueous dilutions containing the respective compounds in an amount corresponding to 50 g/are of the surface of the soil in the planter was uniformly sprayed onto the surface of the soil. Then, the planter was kept in a glass house under the predetermined conditions for 25 days, and then the state of the plants in the planter was observed, and the herbicidal effect was evaluated by the following standards:

| Standards | Result of observation |
|---|---|
| 0 | without any herbicidal effect |
| 1 | herbicidal effect of 20% |
| 2 | herbicidal effect of 40% |
| 3 | herbicidal effect of 60% |
| 4 | herbicidal effect of 80% |
| 5 | herbicidal effect of 100%. |

Test results are shown in Table 2.

TABLE 2

Herbicidal Test Results of Example 1

| Compound No. | Weeds (refer to footnote) | | | | | | Crop plants (refer to footnote) | | | | |
|---|---|---|---|---|---|---|---|---|---|---|---|
| | 1 | 2 | 3 | 4 | 5 | 6 | 1 | 2 | 3 | 4 | 5 |
| 1 | 1 | 0 | 3 | 5 | 5 | 5 | 0 | 0 | 0 | 4 | 3 |
| 2 | 2 | 0 | 5 | 5 | 5 | 5 | 0 | 0 | 0 | 2 | 2 |
| 3 | 1 | 1 | 4 | 4 | 5 | 5 | 0 | 0 | 0 | 2 | 2 |
| 4 | 1 | 0 | 5 | 5 | 5 | 5 | 0 | 0 | 0 | 0 | 1 |
| 5 | 0 | 0 | 4 | 5 | 5 | 5 | 0 | 0 | 0 | 0 | 2 |
| 6 | 2 | 2 | 5 | 5 | 5 | 5 | 0 | 0 | 0 | 3 | 3 |
| 7 | 1 | 1 | 4 | 3 | 5 | 5 | 0 | 0 | 0 | 2 | 2 |
| 8 | 0 | 0 | 4 | 4 | 5 | 5 | 0 | 0 | 0 | 3 | 2 |
| 9 | 1 | 0 | 4 | 3 | 5 | 5 | 0 | 0 | 0 | 0 | 1 |
| 10 | 1 | 0 | 5 | 4 | 5 | 5 | 0 | 0 | 0 | 0 | 1 |
| 11 | 0 | 0 | 4 | 3 | 3 | 3 | 0 | 0 | 0 | 2 | 1 |
| 12 | 3 | 4 | 5 | 5 | 5 | 5 | 0 | 0 | 0 | 2 | 2 |
| 13 | 3 | 0 | 5 | 4 | 5 | 5 | 0 | 0 | 0 | 3 | 2 |
| 14 | 1 | 0 | 5 | 5 | 5 | 5 | 0 | 0 | 0 | 4 | 3 |
| 15 | 3 | 0 | 3 | 4 | 5 | 5 | 0 | 0 | 0 | 2 | 1 |
| 16 | 2 | 0 | 5 | 5 | 4 | 5 | 0 | 0 | 0 | 1 | 3 |
| 17 | 1 | 0 | 5 | 5 | 4 | 5 | 0 | 0 | 0 | 0 | 3 |
| 18 | 0 | 0 | 3 | 4 | 3 | 4 | 0 | 0 | 0 | 0 | 1 |
| 19 | 1 | 0 | 4 | 3 | 5 | 5 | 0 | 0 | 0 | 1 | 2 |
| 20 | 2 | 3 | 5 | 5 | 5 | 5 | 0 | 0 | 0 | 5 | 5 |
| 21 | 2 | 3 | 5 | 5 | 5 | 5 | 0 | 0 | 0 | 4 | 4 |
| 22 | 3 | 4 | 5 | 5 | 5 | 5 | 0 | 0 | 0 | 4 | 5 |
| 23 | 2 | 2 | 5 | 5 | 5 | 5 | 0 | 0 | 0 | 3 | 5 |
| 24 | 2 | 5 | 5 | 5 | 5 | 5 | 0 | 0 | 1 | 2 | 5 |
| 25 | 1 | 5 | 5 | 5 | 5 | 5 | 0 | 0 | 0 | 5 | 5 |
| 26 | 4 | 5 | 5 | 5 | 5 | 5 | 0 | 1 | 0 | 3 | 5 |
| 27 | 1 | 3 | 4 | 5 | 5 | 5 | 0 | 0 | 2 | 1 | 2 |
| 28 | 1 | 1 | 4 | 3 | 5 | 5 | 0 | 0 | 0 | 2 | 2 |
| 29 | 0 | 0 | 4 | 3 | 3 | 3 | 0 | 0 | 0 | 2 | 1 |
| | | | | | | | 0 | 0 | 0 | 5 | 3 |
| 30 | 3 | 3 | 5 | 5 | 5 | 5 | 0 | 0 | 0 | 5 | 4 |
| 31 | 1 | 1 | 4 | 4 | 5 | 5 | 0 | 0 | 0 | 4 | 4 |
| 32 | 2 | 2 | 4 | 4 | 4 | 5 | 0 | 0 | 0 | 4 | 3 |
| 33 | 1 | 1 | 4 | 4 | 5 | 4 | 0 | 0 | 0 | 4 | 4 |
| 34 | 2 | 2 | 4 | 4 | 5 | 4 | 0 | 0 | 0 | 4 | 4 |
| 35 | 2 | 2 | 4 | 5 | 4 | 5 | 0 | 0 | 0 | 4 | 4 |
| 36 | 1 | 1 | 4 | 4 | 4 | 4 | 0 | 0 | 0 | 4 | 3 |
| 37 | 2 | 3 | 5 | 5 | 4 | 5 | 0 | 0 | 0 | 4 | 4 |
| | 1 | 2 | 4 | 4 | 5 | 5 | 0 | 0 | 0 | 3 | 3 |
| 38 | 1 | 2 | 4 | 4 | 4 | 4 | 0 | 0 | 0 | 3 | 3 |
| | 1 | 1 | 4 | 4 | 5 | 5 | 0 | 0 | 0 | 3 | 3 |
| 39 | 3 | 3 | 5 | 5 | 5 | 5 | 0 | 0 | 0 | 5 | 4 |
| 40 | 1 | 2 | 5 | 5 | 4 | 5 | 0 | 0 | 0 | 4 | 3 |
| 41 | 3 | 3 | 5 | 5 | 5 | 4 | 0 | 0 | 0 | 4 | 4 |
| 42 | 2 | 3 | 5 | 5 | 4 | 5 | 0 | 0 | 0 | 4 | 3 |
| 43 | 1 | 2 | 4 | 5 | 4 | 4 | 0 | 0 | 0 | 4 | 3 |
| 44 | 5 | 5 | 5 | 5 | 5 | 5 | 1 | 2 | 1 | 5 | 5 |
| 45 | 3 | 3 | 5 | 5 | 5 | 5 | 1 | 1 | 1 | 4 | 4 |
| 46 | 2 | 2 | 4 | 4 | 5 | 5 | 0 | 0 | 0 | 4 | 4 |
| 47 | 1 | 1 | 4 | 5 | 4 | 5 | 0 | 0 | 0 | 4 | 3 |
| 48 | 1 | 1 | 4 | 5 | 5 | 4 | 0 | 0 | 0 | 4 | 3 |
| 49 | 1 | 1 | 4 | 5 | 4 | 5 | 0 | 0 | 0 | 4 | 4 |
| 50 | 1 | 1 | 4 | 4 | 5 | 4 | 0 | 0 | 0 | 4 | 4 |
| 51 | 1 | 1 | 4 | 4 | 4 | 4 | 0 | 0 | 0 | 3 | 3 |

TABLE 2-continued

Herbicidal Test Results of Example 1

| Compound No. | Weeds (refer to footnote) | | | | | | Crop plants (refer to footnote) | | | | |
|---|---|---|---|---|---|---|---|---|---|---|---|
| | 1 | 2 | 3 | 4 | 5 | 6 | 1 | 2 | 3 | 4 | 5 |
| Control | 0 | 0 | 0 | 0 | 0 | 0 | 0 | 0 | 0 | 0 | 0 |

Note:
Name of Weed and Crop Plant
Weed 1: *Echinochloa crus-galli*
Weed 2: *Poa annua*
Weed 3: *Chenopodium album*
Weed 4: *Cardamine flexuosa*
Weed 5: *Portulaca oleracea*
Weed 6: *Stellaria media*
Crop plant 1: Rice plant
Crop plant 2: Wheat
Crop plant 3: Maize
Crop plant 4: Cucumber
Crop plant 5: Tomato

EXAMPLE 2

Herbicidal Test by Application of Candidate Herbicide onto Plants at their initial stage of growing Each predetermined amount of the seeds of the plants to be tested was sown onto the soil in the same manner as in Example 1, and when the plants reached to their 1 to 2 leaf-stage, each of the aqueous dilutions containing the respective compounds in an amount corresponding to 50 g/are of the surface of the soil in the planter was uniformly sprayed onto the foliage and the surface of the soil. The planter was kept thereafter in a glass house controlled under predetermined conditions for 25 days and then the state of the plants was observed and the herbicidal effect of each compound was evaluated on the same standard shown in Example 1. The results are shown in Table 3.

As are seen in Tables 2 and 3, almost all the present compounds showed excellent herbicidal activity, particularly to the board-leaved weeds as *Chenopodium album*, *Cardamine flexuosa*, *Portulaca orelacea* and *Stellaria media* when applied to their seeds in the soil or at the initial stage of foliar development thereof, without giving any serious phytotoxicity to crop plants such as rice, wheat and maize.

TABLE 3

Herbicidal Test Results of Example 2: (Foliar Application)

| Compound No. | Weeds | | | | | | Crop plants | | | | |
|---|---|---|---|---|---|---|---|---|---|---|---|
| | 1 | 2 | 3 | 4 | 5 | 6 | 1 | 2 | 3 | 4 | 5 |
| 1 | 2 | 2 | 5 | 5 | 5 | 5 | 0 | 0 | 0 | 4 | 3 |
| 2 | 4 | 3 | 5 | 5 | 5 | 5 | 0 | 0 | 0 | 1 | 2 |
| 3 | 2 | 1 | 4 | 5 | 5 | 5 | 0 | 0 | 0 | 2 | 2 |
| 4 | 2 | 2 | 5 | 5 | 5 | 5 | 0 | 0 | 0 | 0 | 1 |
| 5 | 0 | 0 | 4 | 5 | 5 | 5 | 0 | 0 | 0 | 0 | 2 |
| 6 | 1 | 1 | 5 | 5 | 5 | 5 | 0 | 0 | 0 | 3 | 3 |
| 7 | 0 | 0 | 4 | 5 | 5 | 5 | 0 | 0 | 0 | 2 | 2 |
| 8 | 0 | 1 | 2 | 5 | 2 | 5 | 0 | 0 | 0 | 0 | 2 |
| 9 | 2 | 1 | 4 | 3 | 5 | 5 | 0 | 0 | 0 | 1 | 1 |
| 10 | 3 | 2 | 5 | 4 | 5 | 5 | 0 | 0 | 0 | 1 | 1 |
| 11 | 0 | 1 | 2 | 4 | 4 | 5 | 0 | 0 | 0 | 0 | 0 |
| 12 | 3 | 2 | 5 | 5 | 5 | 5 | 0 | 0 | 0 | 0 | 2 |
| 13 | 2 | 1 | 5 | 5 | 5 | 5 | 0 | 0 | 0 | 1 | 3 |
| 14 | 3 | 0 | 4 | 5 | 5 | 5 | 0 | 0 | 0 | 2 | 4 |
| 15 | 3 | 0 | 4 | 3 | 5 | 5 | 0 | 0 | 0 | 1 | 3 |
| 16 | 2 | 1 | 5 | 5 | 5 | 5 | 0 | 0 | 0 | 3 | 3 |
| 17 | 0 | 0 | 5 | 4 | 5 | 5 | 0 | 0 | 0 | 1 | 2 |
| 18 | 0 | 0 | 4 | 3 | 3 | 5 | 0 | 0 | 0 | 0 | 2 |
| 19 | 3 | 0 | 4 | 2 | 3 | 5 | 0 | 0 | 0 | 2 | 4 |
| 20 | 1 | 2 | 5 | 5 | 5 | 5 | 0 | 0 | 1 | 5 | 5 |
| 21 | 2 | 2 | 5 | 5 | 5 | 5 | 0 | 0 | 0 | 4 | 4 |
| 22 | 1 | 1 | 5 | 5 | 5 | 5 | 0 | 0 | 0 | 3 | 5 |
| 23 | 2 | 3 | 5 | 5 | 5 | 5 | 0 | 0 | 0 | 3 | 5 |
| 24 | 3 | 1 | 5 | 5 | 5 | 5 | 0 | 0 | 0 | 2 | 5 |
| 25 | 1 | 2 | 5 | 5 | 5 | 5 | 0 | 0 | 0 | 5 | 5 |
| 26 | 3 | 5 | 5 | 5 | 5 | 5 | 0 | 1 | 3 | 3 | 5 |
| 27 | 2 | 5 | 5 | 5 | 5 | 5 | 0 | 0 | 3 | 4 | 3 |
| 28 | 0 | 1 | 2 | 5 | 2 | 5 | 0 | 0 | 0 | 0 | 2 |
| 29 | 0 | 1 | 2 | 4 | 4 | 5 | 0 | 0 | 0 | 1 | 2 |
| | 1 | 3 | 5 | 5 | 5 | 5 | 0 | 0 | 0 | 4 | 4 |
| 30 | 2 | 2 | 5 | 5 | 5 | 5 | 0 | 0 | 0 | 5 | 5 |
| 31 | 0 | 1 | 5 | 5 | 4 | 4 | 0 | 0 | 0 | 4 | 3 |
| 32 | 1 | 1 | 4 | 4 | 4 | 4 | 0 | 0 | 0 | 4 | 4 |
| 33 | 0 | 0 | 4 | 5 | 4 | 4 | 0 | 0 | 0 | 3 | 3 |
| 34 | 1 | 2 | 4 | 4 | 4 | 5 | 0 | 0 | 0 | 4 | 3 |
| 35 | 0 | 1 | 4 | 4 | 4 | 4 | 0 | 0 | 0 | 4 | 3 |
| 36 | 0 | 0 | 4 | 4 | 4 | 4 | 0 | 0 | 0 | 4 | 3 |
| 37 | 2 | 3 | 5 | 5 | 5 | 4 | 0 | 0 | 0 | 4 | 4 |
| | 0 | 1 | 4 | 4 | 4 | 4 | 0 | 0 | 0 | 3 | 3 |
| 38 | 0 | 0 | 4 | 4 | 4 | 4 | 0 | 0 | 0 | 3 | 3 |
| | 1 | 0 | 4 | 4 | 4 | 4 | 0 | 0 | 0 | 3 | 3 |
| 39 | 2 | 3 | 5 | 5 | 5 | 5 | 0 | 0 | 0 | 5 | 4 |
| 40 | 1 | 2 | 5 | 5 | 5 | 4 | 0 | 0 | 0 | 4 | 3 |
| 41 | 3 | 3 | 5 | 5 | 5 | 5 | 0 | 0 | 0 | 4 | 4 |
| 42 | 2 | 2 | 5 | 5 | 5 | 5 | 0 | 0 | 0 | 4 | 4 |
| 43 | 0 | 1 | 4 | 5 | 4 | 4 | 0 | 0 | 0 | 4 | 3 |
| 44 | 4 | 5 | 5 | 5 | 5 | 5 | 1 | 2 | 1 | 4 | 4 |
| 45 | 3 | 3 | 5 | 5 | 5 | 5 | 1 | 1 | 0 | 4 | 4 |
| 46 | 2 | 2 | 4 | 4 | 4 | 4 | 0 | 0 | 0 | 4 | 4 |
| 47 | 1 | 1 | 4 | 5 | 4 | 4 | 0 | 0 | 0 | 3 | 3 |
| 48 | 0 | 0 | 4 | 5 | 5 | 4 | 0 | 0 | 0 | 3 | 3 |
| 49 | 0 | 0 | 4 | 4 | 4 | 4 | 0 | 0 | 0 | 3 | 3 |
| 50 | 0 | 0 | 4 | 4 | 4 | 4 | 0 | 0 | 0 | 3 | 3 |
| 51 | 0 | 0 | 4 | 4 | 4 | 4 | 0 | 0 | 0 | 3 | 3 |
| Control | 0 | 0 | 0 | 0 | 0 | 0 | 0 | 0 | 0 | 0 | 0 |

Note:
Names of weeds and crop plants are the same as in Table 2.

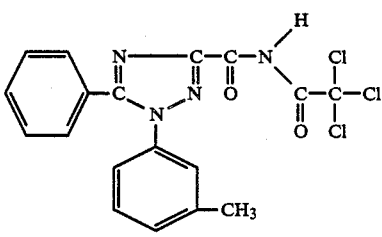

15. A derivative of 1,2,4-triazole according to claim 11, wherein said derivative is 1-(3-methylphenyl)-5-phenyl-triazole-3-thiocarboxamide represented by the formula:
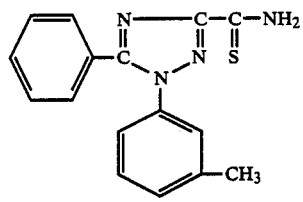

What is claimed is:
1. A herbicidal composition comprising a derivative of 1,2,4-triazole represented by the general formula (I):

(I)

wherein $R^1$ represents a hydrogen atom, halogen atom or $(C_1-C_2)$ alkyl group; $R^2$, represents a hydrogen atom, halogen atom, $(C_1-C_2)$ alkyl group, fluoromethyl group ($-CH_2F$), 3,3,3-trifluoropropyl group, methoxy group, cyano group, methoxymethyl group, methylthio group, methoxycarbonyl group or isopropoxycarbonyl group and $R^3$ represents a thiocarbamoyl group or a group represented by the general formula (II):

(II)

wherein $R^4$ represents a hydrogen atom, $(C_1-C_2)$ alkyl group or hydroxy $(C_1-C_2)$ alkyl group and $R^5$ represents a hydrogen atom, $(C_1-C_2)$ alkyl group, halogeno $(C_1-C_2)$ alkyl group, hydroxy $(C_1-C_2)$ alkyl group, cyanomethyl group, acetyl group, halogenoacetyl group, methoxyacetyl group, amino group, phenyl group, methoxy group, hydroxyl group, (C₂-C₃) alkenyl group, halogeno (C₂-C₃) alkenyl group, isopropylcarbonyl group, methylthiocarbamoyl group or 2-methoxyethyl group, with the proviso that R² is not a hydrogen atom, halogen atom or (C₁-C₂) alkyl group when both of R⁴ and R⁵ represent hydrogen atoms, and a herbicidally acceptable carrier or diluent therefor.

2. A herbicidal composition of claim 1, wherein R¹ represents (C₁-C₂) alkyl group, R² represents a hydrogen atom or (C₁-C₂) alkyl group, R³ represents a thiocarbamoyl group or a group represents by the formula:

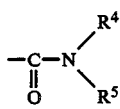

wherein R⁴ represents a hydrogen atom and R⁵ represents acetyl group or halogenoacetyl group.

3. A herbicidal composition of claim 2, wherein the derivative of 1,2,4-triazole is N-acetyl-1-(3-methylphenyl)-5-phenyltriazole-3-carboxamide represented by the formula:

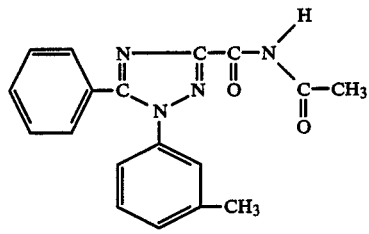

4. A herbicidal composition of claim 2, wherein the derivative of 1,2,4-triazole is N-trichloroacetyl-1-(3-methylphenyl)-5-phenyltriazole-3-carboxamide represented by the formula:

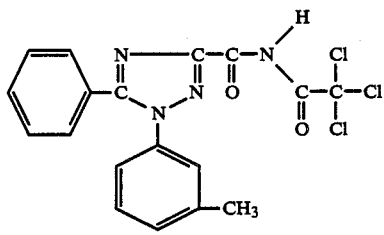

5. A herbicidal composition of claim 2, wherein the derivative of 1,2,4-triazole is 1-(3-methylphenyl)-5-phenyltriazole-3-thiocarboxamide represented by the formula:

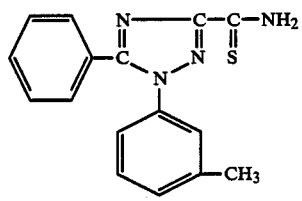

6. A method for controlling the growth of broad-leaved weeds, comprising applying a herbicidally effective amount of a compound of a derivative of 1,2,4-triazole represented by the formula (I):

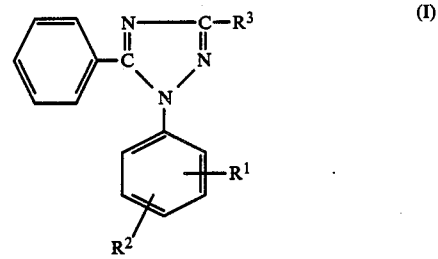

wherein R¹ represents a hydrogen atom, halogen atom or (C₁-C₂) alkyl group; R² represents a hydrogen atom, halogen atom, (C₁-C₂) alkyl group, fluoromethyl group (—CH₂, F), 3,3,3-trifluoropropyl group, methoxy group, cyano group, methoxymethyl group, methylthio group, methoxycarbonyl group or isopropoxycarbonyl group, and R³ represents a thiocarbamoyl group or a group represented by the formula (II):

wherein R⁴ represents a hydrogen atom, (C₁-C₂) alkyl group or hydroxy (C₁-C₂) alkyl group, halogeno (C₁-C₂) alkyl group, hydroxy (C₁-C₂) alkyl group, cyanomethyl group, acetyl group, halogenoacetyl group, methoxyacetyl group, amino group, phenyl group, methoxy group, hydroxyl group, (C₂-C₃) alkenyl group, halogeno (C₂-C₃) alkenyl group, isopropylcarbonyl group, methylthiocarbamoyl group or 2-methoxyethyl group, with the proviso that R² is not a hydrogen atom, halogen atom or (C₁-C₂) alkyl group when both of R⁴ and R⁵ represent hydrogen atoms.

7. A method for controlling the growth of the weeds according to claim 6, wherein said compound is a derivative of 1,2,4-triazole represented by the formula (I) wherein R¹ represents (C₁-C₂) alkyl group, R² represents a hydrogen atom or (C₁-C₂) alkyl group, R³ represents a thiocarbamoyl group or a group represented by the formula:

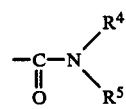

wherein R⁴ represents a hydrogen atom and R⁵ represents acetyl group or halogenoacetyl group.

8. A method for controlling the growth of weeds according to claim 6, wherein said compound is N-acetyl-1-(3-methylphenyl)-5-phenyltriazole-3-carboxamide represented by the formula:

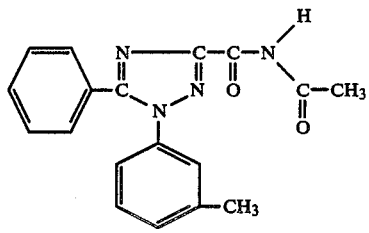

9. A method for controlling the growth of weeds according to claim 6, wherein said compound is N-trichloromethyl-1-(3-methylphenyl)-5-phenyltriazole-3-carboxamide represented by the formula:

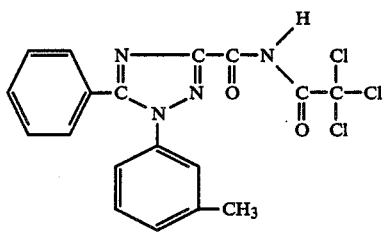

10. A method for controlling the growth of weeds according to claim 6, wherein said compound is 1-(3-methylphenyl)-5-phenyl-triazole-3-thiocarboxamide represented by the formula:

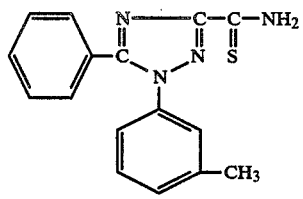

11. A derivative of 1,2,4-triazole represented by the formula (I):

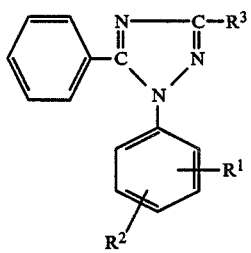

wherein $R^1$ represents a hydrogen atom, halogen atom or ($C_1$–$C_2$) alkyl group; $R^2$ represents a hydrogen atom, halogen atom, ($C_1$–$C_2$) alkyl group, fluoromethyl group (—$CH_2F$), 3,3,3-trifluoropropyl group, methoxy group, cyano group, methoxymethyl group, methylthio group, methoxycarbonyl group or isopropoxycarbonyl group, with the proviso that when one of $R^1$ and $R^2$ is a hydrogen atom the other is bonded at 3-position of benzene ring, and $R^3$ represents a thiocarbamoyl group represented by the formula (II):

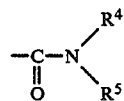

wherein $R^4$ represents a hydrogen atom, ($C_1$–$C_2$) alkyl group or hydroxy ($C_1$–$C_2$) alkyl group and $R^5$ represents a hydrogen atom, ($C_1$–$C_2$) alkyl group, halogeno ($C_1$–$C_2$) alkyl group, hydroxy ($C_1$–$C_2$) alkyl group, cyanomethyl group, acetyl group, halogenoacetyl group, methoxyacetyl group, amino group, phenyl group, methoxy group, hydroxyl group, ($C_2$–$C_3$) alkenyl group, halogeno ($C_2$–$C_3$) alkenyl group, isopropylcarbonyl group, methylthiocarbamoyl group or 2-methoxyethyl group, with the proviso that when both $R^1$ and $R^2$ are hydrogen atoms, $R^3$ represents methylcarbamoyl group, trichloroacetylcarbamoyl group or trifluoroacetylcarbamoyl group, and that $R^2$ is not a hydrogen atom, halogen atom or ($C_1$–$C_2$) alkyl group when both of $R^4$ and $R^5$ represent hydrogen atoms.

12. A derivative of 1,2,4-triazole according to claim 11, wherein said derivative is represented by the formula (I) wherein $R^1$ represents ($C_1$–$C_2$) alkyl group, $R^2$ represents a hydrogen atom or ($C_1$–$C_2$) alkyl group, $R^3$ represents a thiocarbamoyl group or a group represented by the formula:

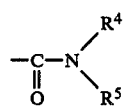

wherein $R^4$ represents a hydrogen atom and $R^5$ represents acetyl group or halogenoacetyl group.

13. A derivative of 1,2,4-triazole according to claim 11, wherein said derivative is N-acetyl-1-(3-methylphenyl)-5-phenyltriazole-3-carboxamide represented by the formula:

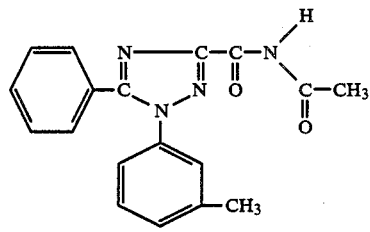

14. A derivative of 1,2,4-triazole according to claim 11, wherein said derivative is N-trichloroacetyl-1-(3-methylphenyl)-5-phenyltriazole-3-carboxamide represented by the formula: